(12) United States Patent
Georgeson et al.

(10) Patent No.: US 11,918,855 B2
(45) Date of Patent: Mar. 5, 2024

(54) ERGONOMICS IMPROVEMENT SYSTEMS HAVING WEARABLE SENSORS AND RELATED METHODS

(71) Applicant: The Boeing Company, Chicago, IL (US)

(72) Inventors: Gary E. Georgeson, Tacoma, WA (US); Brian D. Laughlin, Wichita, KS (US)

(73) Assignee: The Boeing Company, Arlington, VA (US)

( * ) Notice: Subject to any disclaimer, the term of this patent is extended or adjusted under 35 U.S.C. 154(b) by 294 days.

(21) Appl. No.: 17/383,173

(22) Filed: Jul. 22, 2021

(65) Prior Publication Data

US 2023/0021704 A1 Jan. 26, 2023

(51) Int. Cl.
*A63B 24/00* (2006.01)
*A63B 22/00* (2006.01)
*A63B 23/035* (2006.01)

(52) U.S. Cl.
CPC ...... *A63B 24/0062* (2013.01); *A63B 22/0015* (2013.01); *A63B 23/03541* (2013.01); *A63B 24/0006* (2013.01); *A63B 2220/10* (2013.01); *A63B 2220/836* (2013.01); *A63B 2230/60* (2013.01); *A63B 2230/62* (2013.01)

(58) Field of Classification Search
None
See application file for complete search history.

(56) References Cited

U.S. PATENT DOCUMENTS

| | | | |
|---|---|---|---|
| 6,110,130 | A | 8/2000 | Kramer |
| 7,090,576 | B2 | 8/2006 | Herbrich et al. |
| 9,358,426 | B2 | 6/2016 | Aragones et al. |
| 9,610,036 | B1 | 4/2017 | De Sapio et al. |
| 10,065,074 | B1 | 9/2018 | Hoang et al. |
| 10,838,373 | B2 | 11/2020 | Arrowood et al. |
| 11,783,495 | B1 | 10/2023 | Messmore et al. |
| 2001/0020140 | A1 | 9/2001 | Kramer |

(Continued)

FOREIGN PATENT DOCUMENTS

| | | |
|---|---|---|
| CN | 109984747 A | 7/2019 |
| IT | 2019000002215 A1 | 8/2020 |

(Continued)

OTHER PUBLICATIONS

Ihara et al., "Human Movement Instruction System that Utilizes Avatar Overlays Using Stereoscopic Images," WSCG, 2000, 8 pages.

(Continued)

*Primary Examiner* — Thomas S McCormack
(74) *Attorney, Agent, or Firm* — Hanley, Flight & Zimmerman, LLC

(57) ABSTRACT

Ergonomics improvement systems having wearable sensors and related methods. An example ergonomics improvement system includes an encoder system to couple to a limb of a body. The encoder sensor system to generate first outputs in response to movement of the limb relative to the body to determine a position of the limb relative to the body. The system includes a load sensor to generate a second output representative of a load carried by the body and a position sensor to generate a third output representative of a position of a right foot of the body relative to a position of a left foot of the body.

21 Claims, 12 Drawing Sheets

(56) References Cited

U.S. PATENT DOCUMENTS

| | | |
|---|---|---|
| 2003/0163287 A1 | 8/2003 | Vock et al. |
| 2013/0217352 A1 | 8/2013 | Pan et al. |
| 2016/0334762 A1 | 11/2016 | Arrowood et al. |
| 2016/0335574 A1 | 11/2016 | Arrowood et al. |
| 2017/0188894 A1 | 7/2017 | Chang et al. |
| 2018/0279919 A1 | 10/2018 | Bansbach et al. |
| 2018/0369637 A1 | 12/2018 | Hoang et al. |
| 2019/0168120 A1 | 6/2019 | Cossairt |
| 2020/0205673 A1 | 7/2020 | Yi et al. |
| 2020/0276501 A1 | 9/2020 | Cossairt et al. |
| 2020/0281508 A1* | 9/2020 | Ren .................. A61B 5/4519 |
| 2020/0327465 A1 | 10/2020 | Baek et al. |
| 2021/0008413 A1* | 1/2021 | Asikainen ............ G06F 3/0304 |
| 2021/0315488 A1* | 10/2021 | McDaid .................. A61H 3/00 |
| 2022/0003577 A1 | 1/2022 | Evke et al. |
| 2022/0287651 A1 | 9/2022 | Projetti |
| 2022/0374083 A1 | 11/2022 | Tajima et al. |
| 2022/0378349 A1 | 12/2022 | Slepian |
| 2023/0032821 A1 | 2/2023 | Georgeson |
| 2023/0065631 A1 | 3/2023 | Laughlin |
| 2023/0069316 A1 | 3/2023 | Laughlin et al. |
| 2023/0298760 A1 | 9/2023 | Wagner |

FOREIGN PATENT DOCUMENTS

| | | |
|---|---|---|
| JP | 2012183291 A | 9/2012 |
| WO | 2019112737 A1 | 6/2019 |
| WO | 2020102527 A1 | 5/2020 |
| WO | 2021077093 A1 | 4/2021 |
| WO | 2021095493 A1 | 5/2021 |

OTHER PUBLICATIONS

Pinho, "The Use of Thermal Infra-red Imaging to Reveal Muscle Injuries Caused by Physically Demanding Jobs in Industrial Operations," Faculdade de Engenharia da Universidade do Porto, Sep. 2016, 119 pages.

European Patent Office, "Extended European Search Report", issued in connection with European Patent Application No. 22183797.4 dated Dec. 9, 2022, 8 pages.

Baldwin et al., "Kirigami Strain Sensors Microfabricated From Thin-Film Parylene C", Journal of Microelectromechanical Systems, vol. 2, No. 6, Dec. 2018, 7 pages.

European Patent Office, "Extended European Search Report", issued in connection with application No. 22183800.6 dated Jan. 17, 2023, 18 pages.

Wang et al., "Topological design of carbon nanotube-based nanocomposites for strain sensing" Behavior and Mechanics of Multifunctional Materials XIII, Mar. 29, 2019, 9 pages.

Groeger et al., "LASEC: Instant Fabrication of Stretchable Circuits Using a Laser Cutter", CHI '19: Proceedings of the 2019 CHI Conference on Human Factors in Computing Systems, May 2019, 14 pages.

Farhangdoust et al., "Auxetic MEMS Sensor", Proceedings vol. 11379, Sensors and Smart Structures Technologies for Civil, Mechanical, and Aerospace Systems 2020, Apr. 23, 2020, 10 pages.

European Patent Office, "Extended European Search Report", issued in connection with European Patent Application No. 22190359.4 dated Jan. 19, 2023, 8 pages.

European Patent Office, "Extended European Search Report", issued in connection with European Patent Application No. 22190357.8 dated Jan. 30, 2023, 8 pages.

United States Patent and Trademark Office, "Requirement for Restriction / Election," issued in connection with U.S. Appl. No. 17/383,179, dated Jun. 23, 2023, 8 Pages.

United States Patent and Trademark Office, "Non-Final Office Action," issued in connection with U.S. Patent Application No. 17/383, 179, dated Oct. 6, 2023, 11 Pages.

Rammer et al., "Assessment of a markerless motion analysis system for manual wheelcair application," 2018, Journal of NeuroEngineering and Rehabilitation, pp. 1-12 (Year: 2018).

United States Patent and Trademark Office, "Non-Final Office Action," issued in connection with U.S. Appl. No. 17/412,038, dated Oct. 25, 2023, 20 pages.

* cited by examiner

| | POSITION 1 | POSITION 2 | POSITION 3 |
|---|---|---|---|
| SHOULDER CALIBRATION | MOVE ARMS FORWARD AND BACKWARD  902 | RAISE ARMS UPWARD AND DOWNWARD  904 | ROTATE/TWIST ARMS  906 |
| ELBOW CALIBRATION | CURL/BICEP MOTION  SIDE-EXTENDED ARM  908 | BEND ELBOW UPWARD/DOWNWARD  910 | ROTATEE/TWIST ARMS WITH BENT ELBOW  912 |
| WRIST CALIBRATION | BEND WRIST UPWARD/DOWNWARD  914 | BEND WRIST LEFT/RIGHT  916 | TWIST WRIST ABOUT FOREARM  918 |

ERGONOMICS IMPROVEMENT SYSTEMS HAVING WEARABLE SENSORS AND RELATED METHODS

FIELD OF THE DISCLOSURE

This disclosure relates generally to wearable sensors, and more particularly, to ergonomics improvement systems having wearable sensors and related methods.

BACKGROUND

Warehouse and manufacturing users perform various physical and/or repetitive tasks. Such physical tasks can include lifting and/or holding relatively heavy objects for an extended period of time and/or operations that require numerous repetitive motions (e.g., manually sanding a structure by moving a sanding tool in a circular direction a repeated number of times). Performing a physical task can sometimes result in high strain activity.

SUMMARY

An example ergonomics improvement system disclosed herein includes an encoder sensor system to couple to a limb of a body. The example encoder sensor system is to generate first outputs in response to movement of the limb relative to the body to determine a position of the limb relative to the body. The system includes a load sensor to generate a second output representative of a load carried by the body. The example system further includes a position sensor to generate a third output representative of a position of a right foot of the body relative to a position of a left foot of the body.

Another example system disclosed herein to track movement of a limb of a body includes an upper body sensor system structured to be attached to the limb of the body, where the upper body sensor system includes encoders that generate first outputs in response to movements of the limb. The example system includes a lower body sensor system to generate a second output representative of a load carried by the body and third outputs representative of a positioning of a right foot of the body relative to the left foot of the body. The example system also includes a processor to determine a position of the limb relative to the body based on the first outputs. The processor also determines a measured load based on the second outputs. The processor also determines a position of the right foot of the body relative to the left foot of the body based on the third outputs. The processor also compares the determined position of the limb to a position threshold associated with measured load and the detected position of the right foot relative to the left foot. The processor also generates a warning signal in response to determining that the detected position exceeds the position threshold associated with the measured load and the detected position of the right foot relative to the left foot.

An example method to track a limb of a body disclosed herein includes receiving first outputs from an encoder system coupled to the limb. The example system also determines a position of the limb relative to the body based on first outputs received. The example system also receives a second output from a load sensor carried by the body; determining a load of the body based on the received second output. The example system also receives third outputs from a pressure sensor carried by the body. The example system also determines a foot position by detecting a position of a left foot of the body relative to a position of a right foot of the body based on the third outputs from the pressure sensor.

The example system also compares the determined position of the limb and a position threshold associated with the determined load and the determined foot position. The example system also determines if the determined position exceeds the position threshold and generates a warning signal if the determined position exceeds the position threshold.

Figure 1:
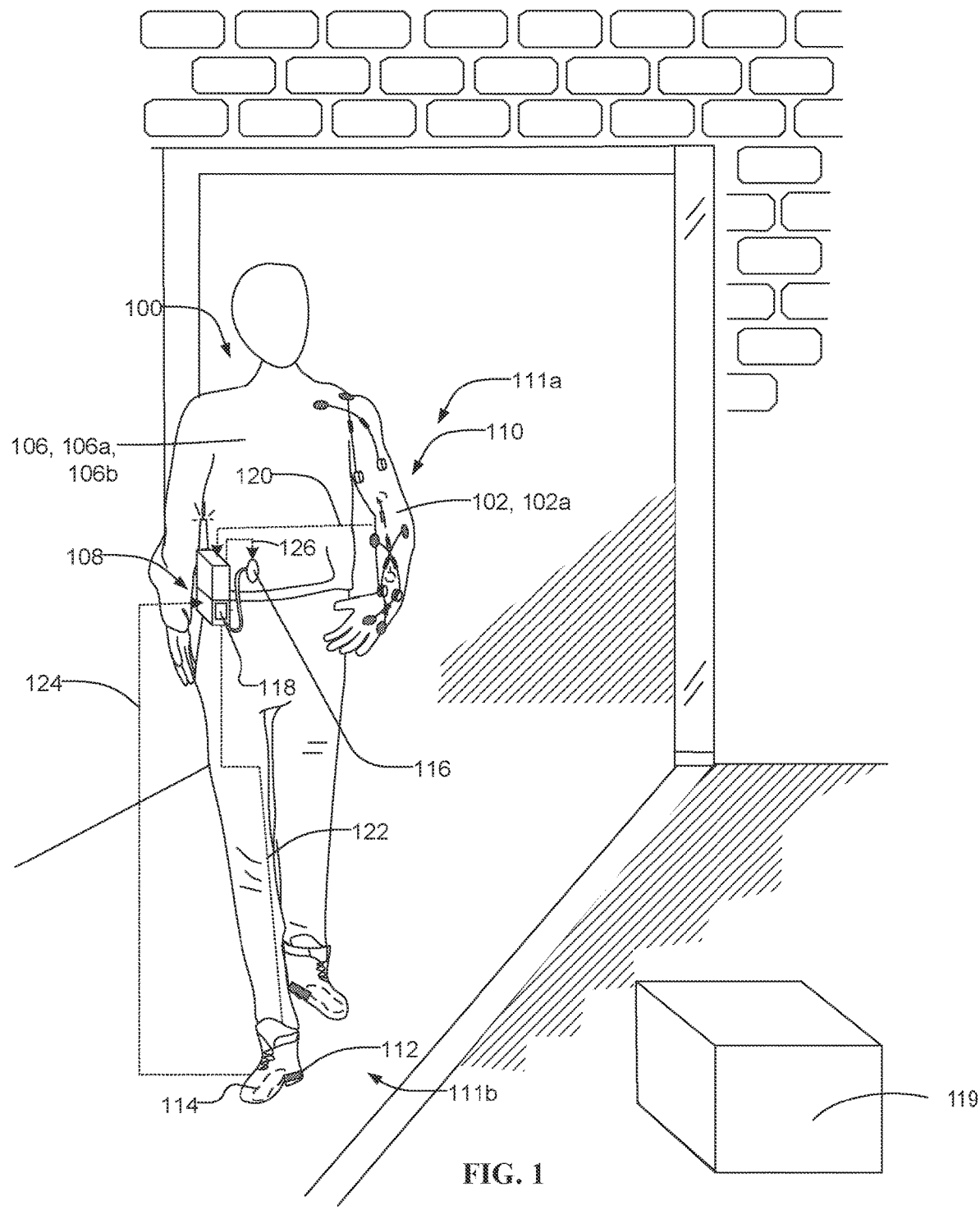
FIG. 1 is an example ergonomics improvement system in accordance with teachings disclosed herein.

The figures are not to scale. Instead, the thickness of the layers or regions may be enlarged in the drawings. In general, the same reference numbers will be used throughout the drawing(s) and accompanying written description to refer to the same or like parts. As used in this patent, stating that any part (e.g., a layer, film, area, region, or plate) is in any way on (e.g., positioned on, located on, disposed on, or formed on, etc.) another part, indicates that the referenced part is either in contact with the other part, or that the referenced part is above the other part with one or more intermediate part(s) located therebetween. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Stating that any part is in "contact" with another part means that there is no intermediate part between the two parts. Although the figures show layers and regions with clean lines and boundaries, some, or all of these lines and/or boundaries may be idealized. In reality, the boundaries and/or lines may be unobservable, blended, and/or irregular.

Descriptors "first," "second," "third," etc. are used herein when identifying multiple elements or components which may be referred to separately. Unless otherwise specified or understood based on their context of use, such descriptors are not intended to impute any meaning of priority, physical order, or arrangement in a list, or ordering in time but are merely used as labels for referring to multiple elements or components separately for ease of understanding the disclosed examples. In some examples, the descriptor "first" may be used to refer to an element in the detailed description, while the same element may be referred to in a claim with a different descriptor such as "second" or "third." In such instances, it should be understood that such descriptors are used merely for ease of referencing multiple elements or components.

DETAILED DESCRIPTION

Manufacturing operations often necessitate users to perform various types of repetitive physical tasks and/or lift objects that are relatively heavy. Performing repetitive physical tasks during certain manufacturing operations can cause undesired risk to operators performing such repetitive physical tasks. For example, performing physical tasks repetitively can result in muscle and/or tendon fatigue over time. Muscle fatigue can reduce a strength of a muscle and/or tendon fatigue can reduce structural capacity of a tendon.

To improve ergonomic awareness, ergonomics improvement systems have been developed to monitor and/or quantify musculoskeletal performance during repeated performance of a physical task or manufacturing operation. Generally, existing technologies are focused on gathering posture and/or movement information for treating injuries. For instance, some known systems monitor musculoskeletal performance using sensors to capture data during a repetitive motion. One known system simulation of a person performing the physical tasks over a number of cycles is run by a computer system using the musculoskeletal model for the person and at least one of the task performance data and task description data. The computer simulated model can be used to track motion and/or analyze the detected motion. To capture data for use with a simulated model, some known ergonomics improvement systems employ one or more sensors. The sensors can sense force and/or motion. However, the sensors of these known ergonomics improvement systems do not detect or sense stress and/or strain applied to one or more joints (e.g., a shoulder joint, an elbow joint, a wrist joint, etc.) of a user performing physical tasks.

Example ergonomics improvement systems disclosed herein employ movement, load measurement and/or feet positioning to determine stress and/or strain that a limb, a joint of a limb, and/or a body is undergoing when a user is performing one or more tasks (e.g., physical tasks involving repetitive motion). To track movement of a limb, detect an angle of a joint of a limb relative to a body (e.g., a torso) and/or otherwise detect stress and/or strain that a joint of a limb is undergoing when a user performs repetitive physical tasks, example ergonomics improvement systems disclosed herein employ one or more wearable sensors. Example wearable sensors disclosed herein, in combination with the ergonomics improvement system, provide a tracking system to track movement of a limb. In some examples, wearable sensors disclosed herein can include example upper body sensor systems, lower body sensor systems, and/or a combination of upper and lower body sensor systems. Data from example wearable sensors disclosed herein (e.g., upper body sensor systems and/or example lower body sensor systems) can be used (e.g., in aggregate or in isolation) to measure one or more of a position of a limb relative to a body, an angle of a joint relative to a body, a rotational position (e.g., twist) of the limb relative to the body, movement of an entire limb relative to a body, and/or any other movement(s) or angle(s) of a limb, body portion (e.g., upper back, lower back, etc.) and/or joint relative to a body.

Example wearable sensors disclosed herein include one or more encoders. In some examples, the one or more example encoders disclosed herein can include string encoders. In some examples, one or more example encoders disclosed herein can include angle or rotary encoders. In some examples, example wearable sensors disclosed herein can include any other type of encoder(s). In some examples, ergonomics improvement systems disclosed herein can employ different types of wearable sensors and/or encoders (e.g., string encoders and angle rotational encoders) to track limb movement and/or obtain limb position data. In some examples, example encoders disclosed herein can be attached to one or more limbs of a body and/or can be positioned across one or more joints to measure one or more of limb position(s), joint angle(s), and/or rotational position(s) of a limb relative to a body. For example, the wearable sensors or encoders can be attached to an arm of a user to detect stress on a shoulder and/or elbow of a user. In some examples, the wearable sensors or encoders can be attached to garments, can be formed as a garment (e.g., shirt), and/or be a part of garments (e.g., sleeve, etc.). In some examples, the wearable sensors or encoders can be attached to a leg, a hip, and/or a lower back of a user to detect stress and/or strain at a knee, hip, and/or lower bac, respectively. In some examples, example encoders disclosed herein can be employed in two or more groupings (e.g., pairs) at each joint of a limb to measure or detect a position and/or joint angle of a joint (e.g., a shoulder joint, a wrist joint, etc.) associated with the two or more grouping of encoders.

To measure a load carried by a user and detect feet positioning of a user, example ergonomics improvement systems disclosed herein employ the lower body sensor system. To measure load, example lower body sensor systems disclosed herein can employ load cell, a pressure sensor, and/or any other sensor(s) for measuring load and/or weight. To detect feet positioning during physical tasks, example lower body sensor systems disclosed herein can employ Lidar sensors, pressure pads and/or pressure scan sensors, and/or any other suitable positioning sensor(s). Example lower body sensor systems disclosed herein can be carried and/or housed by footwear (e.g., shoes, work boots, etc.) to be worn by a user performing physical tasks. In some examples, example lower body sensors disclosed herein can be placed on and/or within the sole of the footwear. Data from example lower body sensors disclosed herein can be used in aggregate with data collected from example upper body sensor systems disclosed herein to determine movement and/or a position of a limb. However, in some examples, ergonomics improvement systems disclosed herein can employ example upper body sensor systems disclosed herein without example lower body sensor systems disclosed herein to detect a position of a limb relative to a body and/or a joint angle of a joint.

Figure 5A:
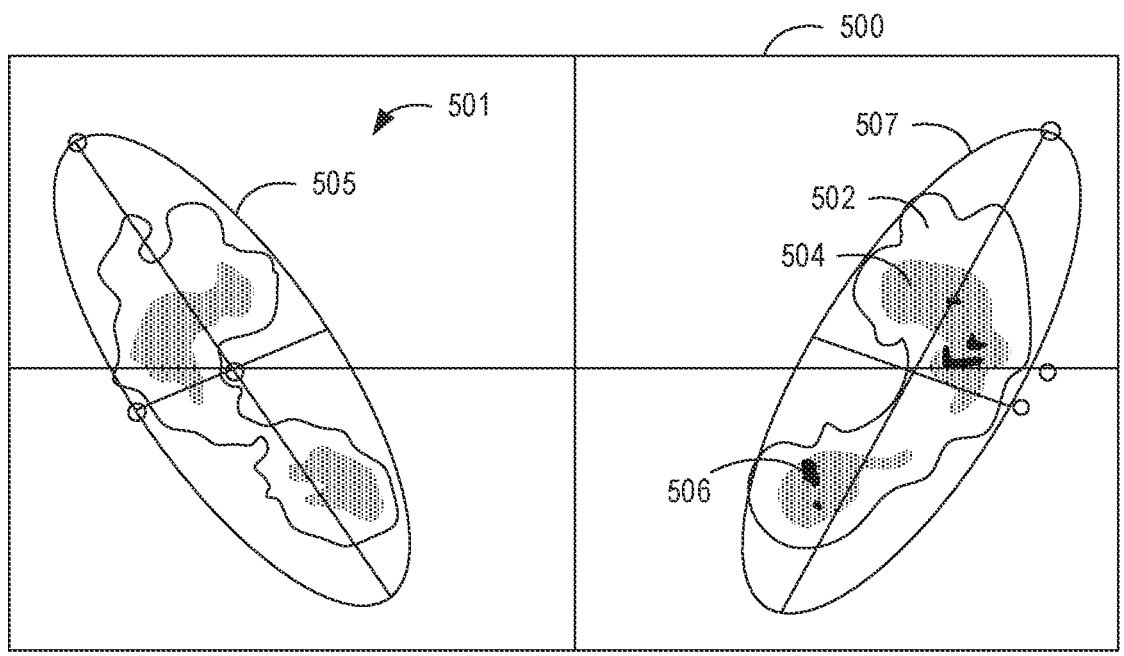
FIGS. 5A and 5B are schematic illustrations of example outputs of the example lower body sensor system of FIG. 4A.

To process data from example wearable sensors disclosed herein (e.g., example upper body and lower body sensor systems), example ergonomics improvement systems disclosed herein employ a controller. In operation, for example, an example controller disclosed herein can receive outputs from the wearable sensors. In some examples, an example controller disclosed herein can compare data from example wearable sensors to a user baseline threshold. For example, the baseline can be predetermined values based on a first condition and a second condition of the user. For example, the first condition can be an amount of load carried by the person and the second condition can be a stance position of a user's feet when detected carrying the load. For example, a baseline threshold for a person carrying a fifty pound weight while standing in a brace position (e.g., the user's feet are in a brace position as shown in FIG. 5A) will not exceed the baseline threshold. However, if the baseline threshold can be exceeded in response to detecting that the user is carrying a fifty pound weight while the user's feet are in a non-brace position (e.g., see FIG. 5B). In some examples, in response to determining that the data of the wearable sensors exceeds the user baseline threshold, example controllers disclosed herein can activate an alarm. Example alarms disclosed herein include, but are not limited to, visual alarms (e.g., a light), audio alarms (e.g., a speaker), haptic feedback (e.g., a vibration), a combination thereof and/or any other alarm(s). In some examples, the type of alarm(s) can be selected based on an environment (e.g., industrial or manufacturing environment) of the user. For example, where the environment can be noisy, busy, or where the tasks being performed should not be interrupted by abrupt or startling alarms, the type of alarm chosen (e.g., haptic feedback) can vary between the options discussed above and/or other types of alarms.

In some examples, example controllers disclosed herein compile outputs from the wearable sensors and transmit the data to a central processing system remotely located from the controller and/or the user. In some such examples, the example central processing system aggregates the data received from the controller and compares the data to a user baseline threshold. In response to determining that the data from the wearable sensors exceeds the user baseline threshold, the example central processing system instructs (e.g., sends a warning signal to) the controller to initiate the example alarm. To provide power to the controller and/or the wearable devices, the example ergonomics improvement system disclosed herein employs a power source. In some examples, an example power source and/or energy generating system can include a battery. In some examples, an example power source can include smart cloths and/or other devices that generate electricity. As used herein, the term "smart cloths" can include motion-powered fabric(s), fabrics that include integrated circuits that can generate power from sweat and/or friction (e.g., movement), frictional forms of human bio-energy, and/or any other fabric or device for generating energy to power one or more of the wearable devices and/or a controller (e.g., fabric piezoelectric nanogenerators that harvest human mechanical motion to energy).

Examples ergonomics improvement systems disclosed herein can track movement of an upper body (e.g., a shoulder, an elbow, a wrist/hand, a forearm, a lower back, etc.) and/or movement of a lower body (e.g., a hip, a knee, a foot, etc.). For example, to track a movement of a leg, one or more example wearable sensors (e.g., encoders) can be attached to (e.g., across) a hip joint, a knee joint, an ankle joint, a lower back, an ankle joint, etc. In some examples, ergonomics improvement systems disclosed herein can track movement of a leg, an arm, a leg and an arm, both arms, both legs, both arms and both legs, an upper back, a lower back, and/or any other limb or portions of a body (e.g., a neck, a lower back, an upper back, etc.) to determine stress and/or strain that a body undergoes when a user performs physical tasks and/or activities. Example ergonomics improvement systems disclosed herein employ one or more sensors (e.g., encoders) that can be positioned adjacent or across joints of the limb (e.g., an arm) to measure limb or joint angle, limb rotation, and/or map a full profile of a motion of the user. In some examples, one or more sensors can be used to indicate limb rotation such as, for example, shoulder-to-arm or forearm-to-wrist rotation. In some examples, one or more sensors can be used in combination to detect, for example, shoulder-to-hand motion and/or position. The sensors disclosed herein can include string encoders, rotary encoders, angle encoders, and/or any combination and/or any other encoder that can detect movement and/or angles of a joint of a limb.

FIG. 1 is an example ergonomics improvement system 100 in accordance with teachings disclosed herein. The ergonomics improvement system 100 of the illustrated example can detect strain and/or stress that a body undergoes when performing specific work tasks that include repetitive physical tasks. To detect strain and/or stress to a body (e.g., or a joint of a body), the ergonomics improvement system 100 of the illustrated example tracks and/or otherwise detects movement of a limb 102 (e.g., an arm 102a) and/or a joint (e.g., a joint angle, a shoulder joint, a wrist joint, an elbow joint) of the limb 102 relative to a body 106 (e.g., a torso 106b of the body 106).

The ergonomics improvement system 100 of the illustrated example includes an example controller 108, an example limb sensor 110, an example load sensor 112, an example position sensor 114, an example warning device 116, and an example power device 118. The limb sensor 110, the load sensor 112, the position sensor 114, and the warning device 116 are communicatively coupled to the controller 108 via, for example, a bus, a physical wire, wireless communication protocol, Bluetooth and/or any other suitable communication protocol(s).

To track and/or detect movement of the limb 102 and/or the joint, the ergonomics improvement system 100 of the illustrated example employs the limb sensor 110 (e.g., a tracking system or an upper body sensor). The limb sensor 110 of FIG. 1 is a tracking system that can be coupled (e.g., directly attached) to the limb 102 and/or the joint of the body 106 to obtain data associated with movement of the limb 102 and/or the joint when a user 106a is performing one or more physical tasks (e.g., physical tasks involving repetitive motion). The ergonomics improvement system 100 includes the limb sensor 110, also referred to as an encoder system, couples to the limb 102 of the body 106 and generates first outputs (e.g., first strain outputs 300 of FIG. 3) in response to movement of the limb 102 relative to the body 106 that are used to determine a position of the limb 102 relative to the body 106. In the illustrated example, the limb sensor 110 is an upper body sensor system 111a that is attached to the arm 102a of the body 106. However, in other examples, the limb sensor 110 can couple to a leg, a shoulder joint, a wrist joint, an elbow joint, knee joint, a hip joint, a lower back and/or any other portion of the body 106. For example, the limb sensor 110 can be coupled or attached to the arm 102a, a leg, a hip, a knee, a neck, a lower back portion, an upper back portion and/or any combination thereof to track movement of one or more limbs and/or joints of the body 106 when the user 106a is performing physical activity. In some examples, multiple limb sensors 110 (e.g., tracking systems, upper body sensors, etc.) can be used to detect movement of multiple limbs or joints of the body 106 when the user 106a is performing a physical activity.

To detect and/or measure a load of the body 106, the ergonomics improvement system 100 of the illustrated example includes the load sensor 112. The load sensor 112 is to generate a second output representative of a load carried by the body 106. The load sensor 112 of FIG. 1 can be a load cell, a pressure sensor, a pressure pad and/or any other sensor(s) for measuring load and/or weight of the body 106.

To detect and/or otherwise determine a stance (e.g., feet positioning) of the user 106a performing a physical task, the ergonomics improvement system 100 of FIG. 1 employs the position sensor 114. The position sensor 114 is to generate a third output (e.g., a third output 500 of FIG. 5A or a third output 500 of FIG. 5B) representative of a position of a right foot of the body 106 relative to a position of a left foot of the body 106. The position sensor 114 of FIG. 1 can detect and/or otherwise determine if the user 106a is standing in a stable or bracing position (e.g., with one foot spaced apart and in front of their other foot) or a non-stable or non-bracing position (e.g., the user 106a standing with the left foot spaced from the right foot substantially in-line with the right foot) when performing the physical task(s). In some examples, by determining the position of each foot of the user 106a via the position sensor 114, the ergonomics improvement system 100 of FIG. 1 can determine if the stance of the user 106a is stable or optimal for carrying a detected load (an object 119 (e.g., a box)). The load sensor 112 and the position sensor 114 of the illustrated example provide a lower body sensor system 111b of the ergonomics improvement system 100.

To determine stress and/or strain that the limb 102 (e.g., a human limb), the joint, and/or the body 106 (e.g., an upper back, a lower back, etc.) undergoes during a physical task, the ergonomics improvement system 100 includes the controller 108. The controller 108 of FIG. 1 is configured to determine whether one or more physical tasks or actions performed by the user 106a if performed with a less desirable or improper motion based on one or more limb sensor outputs 120, load sensor outputs 122, and/or position sensor outputs 124 received by the controller 108.

To warn the user 106a when the controller 108 determines that detected improper or less desirable movement (e.g., non-ergonomic movement) of the user 106a, the ergonomics improvement system 100 of the illustrated example employs the warning device 116. Based on the data provided by the limb sensor 110, the load sensor 112 and/or the position sensor 114 to the controller 108, the controller 108 controls an operation of the warning device 116 (e.g., via a warning signal 126). The warning device 116 of the illustrated example can include, but is not limited to, a light, an audible alarm, haptic feedback and/or any other alarm(s) and/or signal(s). The warning device 116 can be carried by the controller 108 (e.g., a housing of the controller 108), a clothing of the user 106a, attached to the body 106, can be carried or integrated with footwear worn by the user 106a, and/or can be carried by a work hat, gloves, and/or any other tool that can be used by the user 106a.

Alternatively, in some examples, the controller 108 of FIG. 1 can be configured to receive the one or more limb sensor outputs 120, the load sensor outputs 122 and/or the position sensor outputs 124 and transmit or communicate the data (e.g., via transmitter) to a remote location. (e.g., a remote server, a central processing computer, a control room, etc.). A computer at a remote location can process the data provided by the limb sensor 110, the load sensor 112, and/or the position sensor 114 to determine if the data represents user activity that exceeds an activity threshold. The remote computer can then communicate (e.g., send) instructions to the controller 108 to activate the warning device 116 if the remote computer determines that the activity exceeds a threshold.

To provide power to the controller 108 and/or the wearable devices, the example ergonomics improvement system 100 disclosed herein employs the power device 118. The power device 118 of FIG. 1 provides power to the controller 108, the limb sensor 110, the load sensor 112, the position sensor 114, and/or the warning device 116. In some examples, the power device 118 provides power only to the controller 108 and/or the warning device 116. For example, the controller 108, the power device 118, the limb sensor 110, the load sensor 112, the position sensor 114 and the warning device 116 can be electrically coupled via one or more electrical wires. In some examples, the limb sensor 110, the load sensor 112, and the position sensor 114 are powered with dedicated power devices (e.g., batteries) independent from the power device 118 and/or the controller 108. In some examples, the limb sensor 110, the load sensor 112, and/or the position sensor 114 are powered indirectly by the power device 118 through connection(s) with the controller 108. For example, the power device 118 (e.g., a battery) can be electrically coupled with (e.g., to provide power to) the limb sensor 110, the load sensor 112, the position sensor 114, the controller 108 and/or the warning device 116. In some examples, the limb sensor 110, the load sensor 112 and the position sensor 114 have dedicated batteries and do not require power from the power device 118.

The power device 118 of the illustrated example is a battery. In some examples, the term power device 118 can include smart cloths and/or other devices that generate electricity. As used herein, "smart cloths" can include motion-powered fabric(s), fabrics that include integrated circuits that can generate power from sweat and/or frictional movement, frictional forms of human bio-energy, and/or any other fabric or device for generating energy to power the ergonomics improvement system 100 (e.g., one or more of the limb sensor 110, the load sensor 112, the position sensor 114, the warning device 116 and/or a controller 108).

Figure 2A:
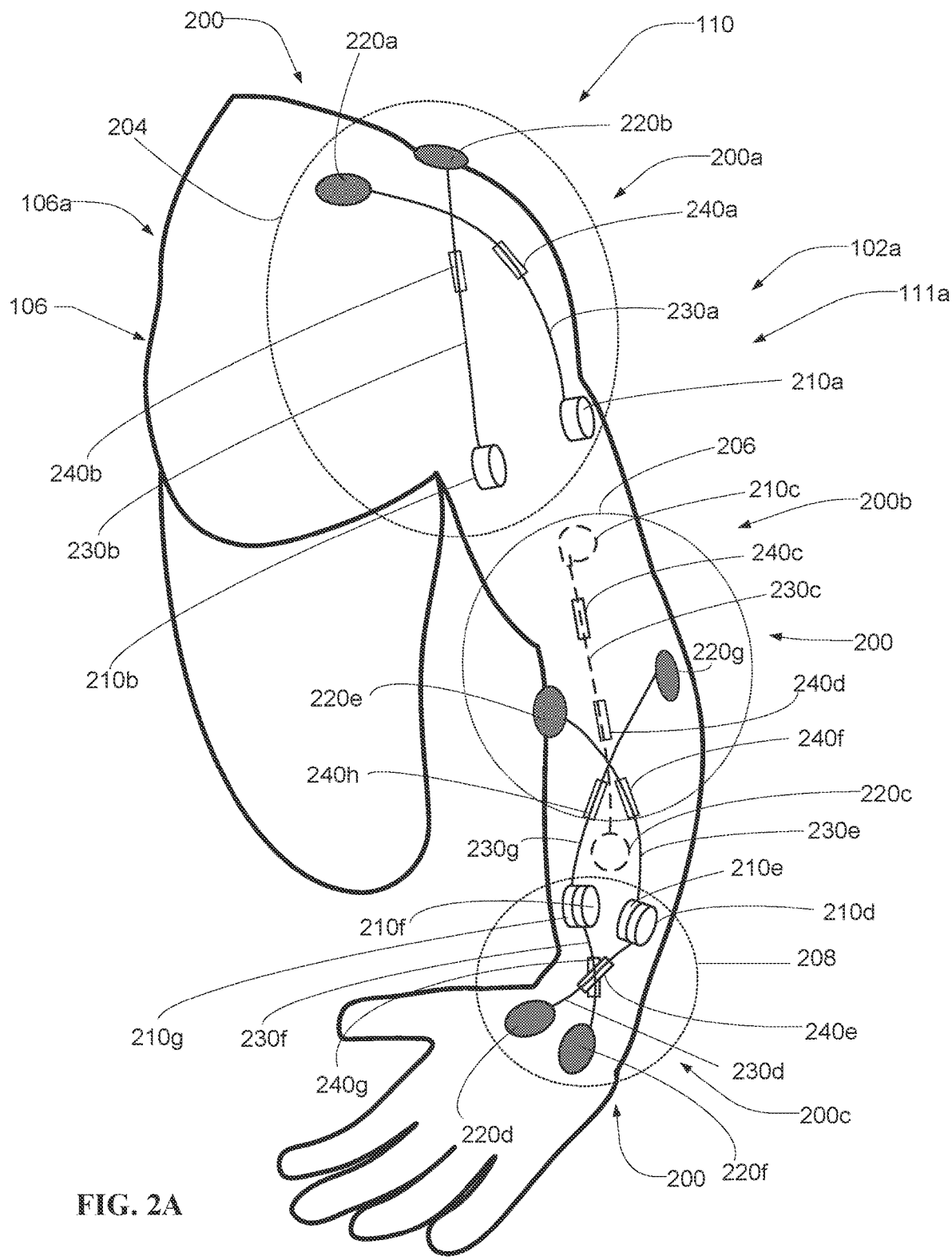
FIG. 2A is an example upper body sensor system of the example ergonomics improvement system of FIG. 1.

FIG. 2A is a perspective view of the limb sensor 110 (e.g., the upper body sensor system 111a) of the example ergonomics improvement system 100 of FIG. 1. The limb sensor 110 of the illustrated example is an encoder system that couples (e.g., attaches) to the arm 102a (or limb) of the body 106. In the illustrated example, the limb sensor 110 includes a plurality of sensor assemblies 200 that generate first outputs to track movement of the limb 102 or arm 102a.

The sensor assemblies 200 of the illustrated example of FIG. 2A include a first sensor assembly 200a (e.g., a first encoder assembly and/or first string encoder assembly) coupled adjacent or proximate a shoulder 204, a second string encoder assembly 200b (e.g., a second encoder assembly) coupled adjacent or proximate an elbow 206, and a third string encoder assembly 200c (e.g., a third encoder assembly) coupled adjacent or proximate a wrist 208. Each of the sensor assemblies 200 detects movement of the user 106a and obtains (e.g., measure or calculate) movement data. Although the example limb sensor 110 of FIG. 2A includes the sensor assemblies 200, in some examples, the limb sensor 110 can include only one sensor assembly (e.g., the second string encoder assembly 200b), two sensor assemblies, more than three sensor assemblies, and/or any other number of sensor assemblies 200.

An example sensor assembly 200 (e.g., an encoder sensor system) of the illustrated example includes string encoders 210a-g, strings 230a-g, and anchors 220a-g. For example, each of the strings 230 (e.g., wire, cable, conductive thread, thread based sensors, metal wire, yarn, rope, etc.) is positioned between a respective one of the string encoders 210 and a respective one of the anchors 220. For instance, a first end of the string 230 is movably coupled to the string encoder 210 and a second end of the string 230 opposite the first end is attached to the body 106 and/or the arm 102a via the anchor 220. To guide and/or maintain an orientation of the strings 230a-g relative to the arm 102a, the sensor assembly 200 of the illustrated example includes sleeves 240a-h. The sleeves 240 slidably receives at least a portion of the respective ones of strings 230a-g when the first end of the string 230 moves (e.g., slides) relative to the encoder 210.

For example, the limb sensor 110 of FIG. 2A includes the first sensor assembly 200a positioned proximate the shoulder 204 to generate first ones of first outputs (e.g., the limb sensor outputs 120) in response to movement of the shoulder 204 that can be used to detect a position of the shoulder 204 relative to the body 106. For example, the first sensor assembly 200a can detect an angle of a joint of the shoulder 204 when the arm 102a moves relative to the body 106. To generate the first ones of the first outputs, the first sensor assembly 200a of the illustrated example includes a first string encoder 210a and a second string encoder 210b. The first string encoder 210a and the second string encoder 210b are attached to a first portion of the arm 102a proximate (e.g., adjacent, or across) the shoulder 204 to detect or track movement of the shoulder 204.

To cause and/or detect an output of the respective first string encoder 210a and the second string encoder 210b, the first sensor assembly 200a includes the first string 230a and the second string 230b, respectively. To anchor the first string 230a, the first sensor assembly 200a includes a first anchor 220a. The first string 230a of the illustrated example is positioned between the first string encoder 210a and the first anchor 220a. Similarly, to anchor the second string 230b, the first sensor assembly 200a includes a second anchor 220b. The second string 230b of the illustrated example is positioned between the second string encoder 210b and the second anchor 220b.

For example, a first end of the first string 230a is (e.g., movably or slidably) coupled to the first string encoder 210a and a second end of the first string 230a opposite the first end is coupled (e.g., fixed) to the body 106 and/or the arm 102a via the first anchor 220a. The first anchor 220a attaches to the body 106 and/or the arm 102a. Likewise, a first end of the second string 230b is (e.g., movably or slidably) coupled to the second string encoder 210b and a second end of the second string 230b opposite the first end is coupled (e.g., fixed) to the body 106 and/or the arm 102a via the second anchor 220b. For example, the second anchor 220b attaches to body 106 and/or the arm 102a. In other words, during movement of the arm 102a, the first end of the first string 230a moves (e.g., pulls) relative to the first string encoder 210a while the second end of the first string 230a remains fixed to the body 106 via the first anchor 220a to output a signal (e.g., a voltage, a current, etc.) of the first string encoder 210a, and the first end of the second string 230b moves (e.g., pulls) relative to the second string encoder 210b while the second end of the second string 230b remains fixed to the body 106 via the second anchor 220b to output a signal (e.g., a voltage, a current, etc.) of the second string encoder 210b. In some examples, the output signal can be proportional to the change in motion (e.g., a quantity) that is to be measured (e.g., movement of the arm 102a). In some examples, a type or amount of an output signal can be generated by a passive sensor and/or an active sensor. For example, the active sensor includes an external power device (e.g., the power device 118) and an excitation signal (e.g., strain gauge), which produces the output signal. A passive sensor, for example, does not need an additional power device (e.g., the power device 118). Instead, the passive sensor generates an output signal in response to an external stimulus.

In the illustrated example, the first sensor assembly 200a is positioned in a crisscross orientation or pattern (e.g., an "X" formation) such that the first string 230a crosses the second string 230b. To maintain or secure the formation of the first string 230a and the second string 230b, the first sensor assembly 200a includes a first guide or first sleeve 240a and a second guide or second sleeve 240b. In some examples, the sleeves 240a-h can be formed as a protective cover and/or stabilization cover (e.g., so a string 230a-g does not move and/or shift). In some examples, the first sleeve 240a and/or the second sleeve 240b can be an attachable cloth, a sleeve made of a protective covering and/or any other sleeve device or cover, etc. In some examples, the first sleeve 240a and/or the second sleeve 240b can be made of cloth, nylon, mesh, plastic, wire, rubber, rubber-like polymers, insulating tubing, and/or any other material(s).

The first sleeve 240a receives at least a portion of the first string 230a and enables the first string 230a to slide within the first sleeve 240a during movement of the limb 102. The second sleeve 240b receives at least a portion of the second string 230b and enables the second string 230b to slide within the second sleeve 240b during movement of the limb 102. The first sleeve 240a and the second sleeve 240b of the illustrated example are spaced apart and attached to the limb 102 (e.g., the arm 102a proximate the shoulder 204). In the illustrated example, the first sleeve 240a is positioned between the first anchor 220a and the first string encoder 210a and the second sleeve 240b is positioned between the second anchor 220b and the second string encoder 210b.

In some examples, the first sensor assembly 200a can include different formations. For example, the first string 230a and the second string 230b can be positioned in parallel, more than one crossing formations (e.g., double crisscross formation) and/or any other orientations. In some examples, using parallel, crossing formations and/or any other orientations allows the sensor assemblies 200a-c to gather different types of data about the movement of the limb 102 in various positions and during various movements. In some examples, one or more of the first string encoder 210a, the second string encoder 210b, the first string 230a, the second string 230b, the first anchor 220a, the second anchor 220b, the first sleeve 240a and/or the second sleeve 240b can be located or positioned on an anterior part of the shoulder 204 and/or a posterior part of the shoulder 204. The first sensor assembly 200a is not limited to the example shown in FIG. 2A. In some examples, the first sensor assembly 200a can include a single sensor assembly (e.g., a first string encoder assembly including the first string encoder 210a, the first string 230a, the first anchor 220a, the first sleeve 240a) or two or more string encoder assemblies.

The second string encoder assembly 200b (e.g., second encoder assembly and/or second string encoder assembly) is positioned proximate (e.g., attached to) the elbow 206 of the limb 102. The second string encoder assembly 200b generates second ones of first outputs (e.g., the limb sensor outputs 120 of FIG. 1) in response to movement of the elbow 206 to detect a position and/or a joint angle of the elbow 206 relative to the body 106. For example, the second string encoder assembly 200*b* can detect a bend angle of the elbow 206. The second string encoder assembly 200*b* includes a third string encoder 210*c*, a third anchor 220*c*, and a third string 230*c*. The third string 230*c* of the illustrated example has a first end (e.g., movably or slidably) coupled to the third string encoder 210*c* and a second end attached (e.g., fixed) to the body 106 and/or the arm 102*a* via the third anchor 220*c*. The third string 230*c* is coupled to the third string encoder 210*c* and moves (e.g., pulls) relative to the third string encoder 210*c* while the second end of the third string 230*c* is fixed to the arm 102*a* via the third anchor 220*c* to output a signal (e.g., a voltage, a current, etc.) of the third string encoder 210*c*. Additionally, to guide and/or secure the third string 230*c*, the second string encoder assembly 200*b* includes a third guide or third sleeve 240*c* and a fourth guide or fourth sleeve 240*d*. The third sleeve 240*c* is located above the elbow 206 (e.g., adjacent a bicep) and the fourth sleeve 240*d* is located below the elbow 206 (e.g., adjacent a forearm). The third sleeve 240*c* and the fourth sleeve 240*d* attach to the arm 102*a* of the user 106*a*. The third sleeve 240*c* and the fourth sleeve 240*d* slidably receive the third string 230*c* to maintain or guide a position of the third string 230*c* relative to the arm 102*a* during movement of the arm 102*a*.

FIG. 2A shows the second string encoder assembly 200*b* located on the posterior of the arm 102*a* (e.g., behind the elbow 206 or backside of the arm 102*a*). The third string 230*c* extends at least partially across the elbow 206 (e.g., across a joint of the elbow). For instance, the third anchor 220*c* is positioned on a first side of the elbow 206 (e.g., adjacent a tricep of the arm 102*a*) and the third string encoder 210*c* is positioned adjacent a second side of the elbow 206 (e.g., adjacent a forearm of the arm 102*a*). In the illustrated example, the third string encoder assembly 200*c* (e.g., the third string 230*c*) is aligned in a straight line across the elbow 206 of the user 106*a*. However, the second string encoder assembly 200*b* is not limited to the location or position shown in FIG. 2A. For example, the second string encoder assembly 200*b* can be located on a side of the arm 102*a* and/or an anterior of the elbow 206 (e.g., on a front side of the arm 102*a*). The string encoder assemblies 200*a*-*c* can be placed in different locations and/or positions to collect data including different angles, from a different group of muscles, for a different type of movement that would not be able to be monitored otherwise from certain positions of the sensor assemblies 200*a*-*c*. For example, one or more sensors 200*a*-*c* can be positioned on a lower back to measure movement or strain of a lower back, an upper back, a neck area, a foot, an ankle, a knee, etc.

The third string encoder assembly 200*c* (e.g., third encoder assembly and/or third string encoder assembly) generates third ones of the first outputs (e.g., the limb sensor outputs 120 of FIG. 1) in response to movement of the wrist 208 to detect a position or angle of the wrist 208 relative to the body 106. To generate or detect the third ones of the first outputs, the third string encoder assembly 200*c* of the illustrated example includes a fourth string encoder 210*d*, a fifth string encoder 210*e*, a sixth string encoder 210*f* and a seventh string encoder 210*g*. Specifically, the fourth string encoder 210*d* and the fifth string encoder 210*e* are arranged as double encoders. Likewise, the sixth string encoder 210*f* and the seventh string encoder 210*g* are arranged as double encoders. In other words, the fourth string encoder 210*d* is attached or coupled to the fifth string encoder 210*e* and the sixth string encoder 210*f* is attached or coupled to the seventh string encoder 210*g*.

To operate the string encoders 210*d*-*g*, the third string encoder assembly 200*c* includes a fourth string 230*d*, a fifth string 230*e*, a sixth string 230*f*, and a seventh string 230*g* coupled to respective ones of the string encoders 210*d*-*g*. For example, the fourth string 230*d* is positioned between the fourth string encoder 210*d* and a fourth anchor 220*d*. For example, a first end of the fourth string 230*d* is (e.g., movably or slidably) coupled to the fourth string encoder 210*d* and the second end of the fourth string 230*d* is coupled (e.g., fixed) to the arm 102*a* via the fourth anchor 220*d*. The fifth string 230*e* is positioned between the fifth string encoder 210*e* and a fifth anchor 220*e*. For example, a first end of the fifth string 230*e* is (e.g., movably or slidably) coupled to the fifth string encoder 210*e* and the second end of the fifth string 230*e* is coupled (e.g., fixed) to the arm 102*a* via the fifth anchor 220*e*. Similarly, the sixth string 230*f* is positioned between the sixth string encoder 210*f* and a sixth anchor 220*f*. For example, a first end of the sixth string 230*f* is (e.g., movably or slidably) coupled to the sixth string encoder 210*f* and the second end of the sixth string 230*f* is coupled (e.g., fixed) to the arm 102*a* via the sixth anchor 220*f*. The seventh string 230*g* is positioned between the seventh string encoder 210*g* and a seventh anchor 220*g*. For example, a first end of the seventh string 230*g* is (e.g., movably or slidably) coupled to the seventh string encoder 210*g* and the second end of the seventh string 230*g* is coupled (e.g., fixed) to the arm 102*a* via the seventh anchor 220*g*.

Thus, the fourth string encoder 210*d* and the fifth string encoder 210*e* operate as a double encoder and output a summation signal (e.g., a voltage, a current, etc.) based on a position of the fourth string 230*d* and the fifth string 230*e*. Thus, the fourth and fifth string encoders 210*d*, 210*d* of the illustrated example output a single output. Similarly, the sixth string encoder 210*f* and the seventh string encoder 210*g* operate as a double encoder and output a summation signal (e.g., a voltage, a current, etc.) based on a position of the sixth string 230*f* and the seventh string 230*g*. Thus, the sixth and seventh string encoders 210*f*, 210*g* of the illustrated example output a single output.

To maintain and/or guide the fourth string 230*d*, the third string encoder assembly 200*c* includes a fifth sleeve 240*e*. The fifth sleeve 240*e* of the illustrated example slidably receives at least a portion of the fourth string 230*d* and/or maintains a position or orientation of the fourth string 230*d* relative to the arm 102*a*. The fifth sleeve 240*e* is positioned between the fourth string encoder 210*d* and the fourth anchor 220*d*. To maintain and/or guide the fifth string 230*e*, the third string encoder assembly 200*c* includes a sixth sleeve 240*f*. The sixth sleeve 240*f* of the illustrated example slidably receives at least a portion of the fifth string 230*e* and/or maintains a position or orientation of the fifth string 230*e* relative to the arm 102*a*. The sixth sleeve 240*f* is positioned between the fifth encoder 210*e* and the fifth anchor 220*e*. To maintain and/or guide the sixth string 230*f*, the third string encoder assembly 200*c* includes a seventh sleeve 240*g*. The seventh sleeve 240*g* of the illustrated example slidably receives at least a portion of the sixth string 230*f* and/or maintains a position or orientation of the sixth string 230*f* relative to the arm 102*a*. The seventh sleeve 240*g* is positioned between the sixth string encoder 210*f* and the sixth anchor 220*f*. To maintain and/or guide the seventh string 230*g*, the third string encoder assembly 200*c* includes an eighth sleeve 240*h*. The eighth sleeve 240*h* of the illustrated example slidably receives at least a portion of the seventh string 230g and/or maintains a position or orientation of the seventh string 230g relative to the arm 102a. The eighth sleeve 240h is positioned between the seventh string encoder 210g and the seventh anchor 220g.

The third string encoder assembly 200c is positioned in a double crossing "U" formation. For example, the fourth string 230d crosses or overlaps the sixth string 230f, and the fifth string 230e crosses or overlaps the seventh string 230g. The sleeves 240e-h maintain the orientation of the strings 230f-g relative to the arm 102a during movement of the arm 102a, wrist 208 and/or forearm. In some examples, the third string encoder assembly 200c can also include different formations such that the strings 230f-g are oriented in parallel relative to each other and/or any other formation. Also, in the illustrated example, the third string encoder assembly 200c is positioned on a front or anterior portion of the arm 102a, wrist 208 and/or forearm. However, in some examples, the third string encoder assembly 200c can be located on the posterior of the arm 102a and/or can extend between the anterior and the posterior of the arm 102a, wrist 208 and/or forearm. In some examples, a first portion (e.g., the fifth string encoder 210e, the fifth string 230e, the fifth anchor 220e, the seventh string encoder 210g, the seventh string 230g, the seventh anchor 220g) of the third string encoder assembly 200c can be located on a posterior side of the arm 102a, the wrist 208 and/or the forearm and a second portion (e.g., the fourth string encoder 210d, the fourth string 230d, the fourth anchor 220d, the sixth string encoder 210f, the sixth string 230f, the sixth anchor 220f) of the third string encoder assembly 200c can be located on the anterior of the arm 102a, the wrist 208 and/or the forearm.

The example sensor assemblies 200 (e.g., the string encoders 210a-g, the anchors 220a-g, and/or the sleeves 240a-h) can be attached (e.g., directly) to the body 106 via adhesive. In some examples, the adhesive can include a plastic, tape, glue, latex strip, and/or any other adhesive. In some examples, the adhesive(s) can attach at one point to the body 106 of the user 106a. In some examples, the adhesive (s) can attach at another point to the sensor assemblies 200. In some examples, the sensor assembly 200 can be implemented on cloth, woven fabric, or other material or apparel that can be worn by the user 106a. For example, the sensor assemblies 200 can be attached to a sleeve or wearable device that can be removably worn by the user 106a. An example of the wearable device can include, but is not limited to, a sleeve, a shirt, an attachable cloth, a sleeve, a rubber, or flexible sleeve. The sensor assembly 200 can be permanently attached to the cloth or piece of apparel and/or it can be removal and reattachable. In other examples, the sensor assemblies 200 are directly attached to the arm 102a of the user 106a via removable adhesive.

Figure 2B:
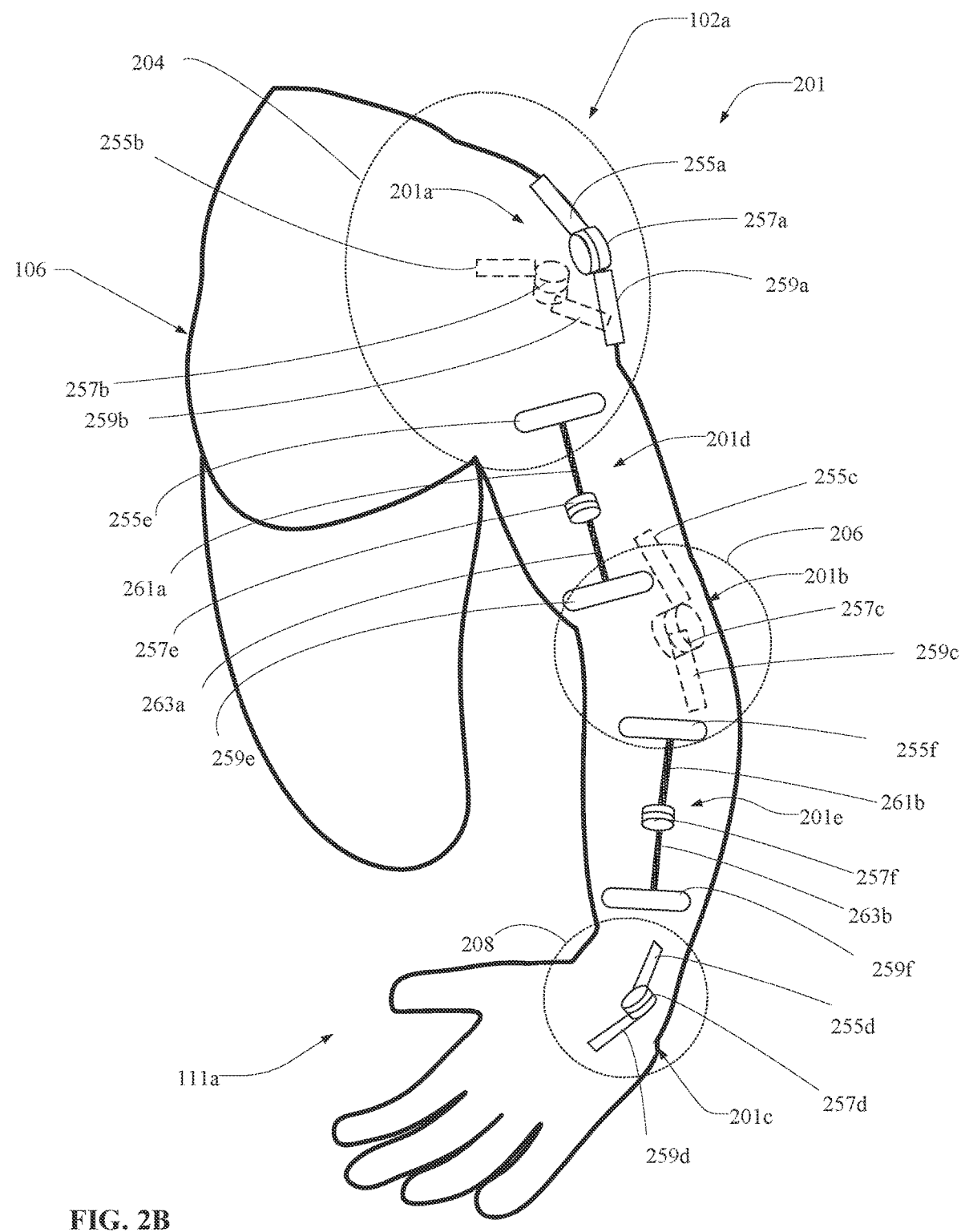
FIG. 2B is another example upper body sensor system disclosed herein that can be used to implement the example ergonomics improvement system of FIG. 1.

FIG. 2B is another example limb sensor 201 (e.g., an encoder assembly) that can be used to implement the limb sensor 110 (e.g., upper body sensor system 111a) of the example ergonomics improvement system 100 of FIG. 1. The limb sensor 201 of the illustrated example is an encoder system that couples (e.g., attaches) to the arm 102a of the body 106. In the illustrated example, the limb sensor 201 includes a plurality of sensor assemblies 201a-e (e.g., encoder assemblies) that generate first outputs. The sensor assemblies 201a-e can be positioned adjacent or across joints of the limb 102 to measure limb or joint angle, limb rotation, and/or obtain a full profile of a motion of the user 106a. The sensor assemblies 201a-e of FIG. 2B include a first sensor assembly 201a coupled adjacent or proximate the shoulder 204, a second sensor assembly 201b coupled adjacent or proximate the elbow 206, and a third sensor assembly 201c coupled adjacent or proximate the wrist 208. In the illustrated example, limb sensor 201 includes a fourth sensor assembly 201d coupled adjacent or proximate the upper arm (e.g., bicep or tricep) and a fifth sensor assembly 201e coupled adjacent or proximate the forearm. For example, the fourth sensor assembly 201d is positioned between the shoulder 204 and the elbow 206 and the fifth sensor assembly 201e is positioned between the wrist 208 and the elbow 206. However, in some examples, the limb sensor 201 does not include the fourth sensor assembly 201d and/or the fifth sensor assembly 201e. Each of the sensor assemblies 201a-e detect movement of the limb 102 of the user 106a and obtain (e.g., measure or calculate) movement data. Although the example limb sensor 201 of FIG. 2B includes the sensor assemblies 201a-e, in some examples, the limb sensor 201 can include only one of the sensor assemblies 201a-e (e.g., the second sensor assembly 201b) and/or any other number of sensor assemblies 201a-e.

The first sensor assembly 201a of FIG. 2B is positioned proximate the shoulder to generate first ones of first outputs in response to movement of the shoulder 204 that can be used to detect a position of the shoulder 204 relative to the body 106. For example, the first sensor assembly 201a can detect a joint angle of the shoulder 204 when the arm 102a moves relative to the body 106. To generate the first ones of the first outputs, the first sensor assembly 201a of the illustrated example includes a first rotary encoder 257a and a second rotary encoder 257b. The first rotary encoder 257a is attached to a first portion of the shoulder 204 (e.g., a side or anterior of the shoulder 204) and the second rotary encoder 257b is attached to a second portion of the shoulder 204 (e.g., a rear or posterior of the shoulder 204 or upper back of the body 106) to track movement or rotation of the shoulder 204. To couple the rotary encoders 257a-b to the body 106, the first sensor assembly 201a includes a first anchor 255a and a second anchor 259a. The first rotary encoder 257a of the illustrated example is positioned between the anchors 255a, 259a. The second rotary encoder 257b is attached to the body 106 via a third anchor 255b and a fourth anchor 259b. The second rotary encoder 257b of the illustrated example is positioned between the anchors 255b, 259b.

The second sensor assembly 201b of FIG. 2B is positioned proximate (e.g., attached to) the elbow 206 of the limb relative to the body 106. The second sensor assembly 201b generates second ones of first outputs in response to movement of the elbow 206 to detect a position and/or joint angle of the elbow 206 relative to the body 106. For example, the second sensor assembly 201b can detect a bend angle and/or rotation of the elbow joint. The second sensor assembly 201b includes a third rotary encoder 257c attached to the body 106 via a fifth anchor 255c and a sixth anchor 259c. The third rotary encoder 257c is attached to a third portion of the arm 102a proximate (e.g., adjacent, or across) the elbow 206 to track movement or rotation of the elbow 206. FIG. 2B shows the second sensor assembly 201b located on the posterior of the arm 102a (e.g., behind the elbow 206 or backside of the arm 102a). The fifth anchor 255c is located above the elbow 206 and the sixth anchor 259c is located below the elbow 206. The third rotary encoder 257c is positioned between the fifth anchor 255c and the sixth anchor 259c. The second sensor assembly 201b is not limited to the location or position shown in FIG. 2B. For example, the second sensor assembly 201b can be located on the inside of the arm 102a and/or an anterior of the elbow 206 (e.g., on a front side of the arm).

The third sensor assembly 201c of FIG. 2B is to generate third ones of the first outputs in response to movement of the wrist 208 to detect a position or angle of the wrist 208 relative to the body 106. To generate or detect the third ones of the first outputs, the third sensor assembly 201c of the illustrated example includes a seventh anchor 255d, a fourth rotary encoder 257d, and an eighth anchor 259d. The fourth rotary encoder 257d is attached to a fourth position of the arm 102a proximate (e.g., adjacent, or across) the wrist 208 to track movement or rotation of the wrist 208. Also, in the illustrated example, the third sensor assembly 201c is positioned on a front or anterior portion of the arm 102a, wrist 208 and/or forearm. However, in some examples, the third sensor assembly 201c can be located on the posterior of the arm 102a and/or can extend between the anterior and the posterior of the arm 102a, wrist 208 and/or forearm.

Additionally, the anchors 255a-c and the anchors 259a-c of FIG. 2B can provide a reference for the respective rotary encoders 257a-c to detect a rotational angle of the arm 102a relative to a reference or initial position (e.g., a zero calibration position). For example, rotation of the arm 102a can cause a first end of the respective anchors 255a-c, 259a-c that is attached to the respective rotary encoders 257a-c to move while a second end of the respective anchors 255a-c, 259a-c remains fixed to the body 106. Such rotational movement of the first end of the anchors 255a-c, 259a-c relative to the second end of the anchors 255a-c, 259a-c enables the respective rotary encoders 257a-c to detect an angular position of the arm 102a.

The fourth sensor assembly 201d generates fourth ones of the first outputs in response to movement of the upper arm 102c (e.g., bicep and/or tricep) to detect a position or angle (e.g., a twist angle) of the upper arm 102c relative to the body 106. To generate or detect the fourth ones of the first outputs, the fourth sensor assembly 201d of the illustrated example includes a fifth rotary encoder 257e. The fifth rotary encoder 257e is attached to a fourth position of the arm 102a proximate (e.g., adjacent, or across) the upper arm 102c to track movement or an angle of the upper arm 102c. The fifth rotary encoder 257e is attached to the arm 102a via a ninth anchor 255e and a tenth anchor 259e. Additionally, to provide a reference for the fifth rotary encoder 257e and/or to enable the fifth rotary encoder 257e to detect a twist angle of an upper portion of the arm 102a, the fourth sensor assembly 201d of FIG. 2B includes a first extension rod 261a and a second extension rod 263a. For example, the first extension rod 261a is positioned between the fifth rotary encoder 257e and the ninth anchor 255e and the second extension rod 263a is positioned between the fifth rotary encoder 257e and the tenth anchor 259e. In other words, the fifth rotary encoder 257e is located in between the first extension rod 261c and the first extension rod 263c. For example, the extension rods 261a, 263a enable the fifth rotary encoder 257e to detect movement, twist, or rotational movement of arm 102a (e.g., the upper arm) relative to the body 106 (e.g., with a greater degree of accuracy). Also, in the illustrated example, the fourth sensor assembly 201d is positioned on a front or anterior portion of the arm 102a. However, in some examples, the fourth sensor assembly 201d can be located on the posterior of the arm 102a.

The fifth sensor assembly 201e of FIG. 2B generates fifth ones of the first outputs in response to movement of the forearm 102e (e.g., space between elbow 206 and wrist 208). For example, the fifth sensor assembly 201e includes a sixth rotary encoder 257f attached to a fifth portion of the arm 102a proximate (e.g., adjacent, or across) the forearm 102e that generates fifth ones of the first outputs to track or detect movement, twist and/or rotation of the forearm 102e relative to the body 106. The sixth rotary encoder 257f is coupled to the arm 102a via an eleventh anchor 255f and a twelfth anchor 259f. A second extension rod 261b is positioned between the sixth rotary encoder 257f and the eleventh anchor 255f and a second extension rod 263b is positioned between the sixth rotary encoder 257f and the twelfth anchor 259f. Also, in the illustrated example, the fifth sensor assembly 201e is positioned on a front or anterior portion of the arm 102a. However, in some examples, the fifth sensor assembly 201e can be located on the posterior of the arm 102a.

The example limb sensor 201 (e.g., the rotary encoders 257a-f, the anchors 255a-f, 259a-f, the extension rods 261a-b, 263a-b) can be attached to the body 106 via adhesive. In some examples, the adhesives can include a woven fabric, a plastic, tape, glue, latex strip, and/or any other type of adhesive. In some examples, the adhesives can include releasable fasteners such as, for example, a hook and loop fastener, Velcro® brand fastener, straps and/or any other releasable fastener. In some examples, the limb sensor 201 can be implemented on a cloth, shirt, sleeve, or other piece of apparel. The rotary encoders 257a-f are rotary encoders, rotary sensors, rotational encoders, rotational sensors, and/or any other sensor measuring rotation of the limb 102.

Figure 3:
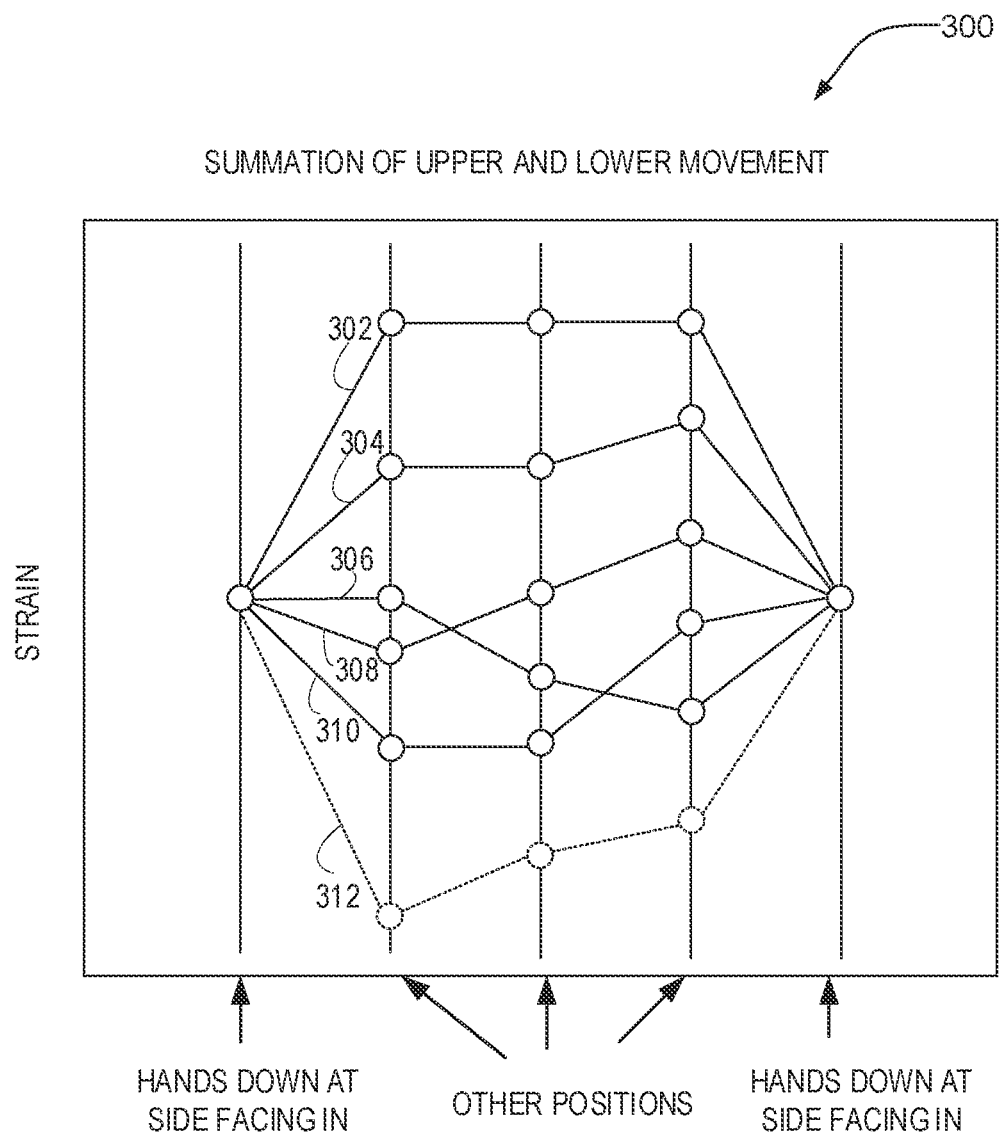
FIG. 3 is an example diagram illustrating example outputs of the example upper body sensor system of FIG. 2A.

FIG. 3 is an example diagram 300 illustrating example outputs of the example sensor assemblies 200 of FIG. 2A. In operation, the first sensor assembly 200a provides first ones of the first outputs (e.g., the limb sensor outputs 120). Specifically, the during movement of the shoulder 204, the first string encoder 210a generates a first strain output 302 based on a position (e.g., a taut condition) of the first string 230a and the second string encoder 210b generates a second strain output 304 based on a position (e.g., a taut condition) of the second string 230b. Based on a position of the elbow 206 (e.g., bent or straight), the third string encoder 210c generates a third strain output 306 based on a position (e.g., a taut condition) of the third string 230c. Based on a position of the hand (e.g., bent or straight at the wrist) and a position of the forearm (e.g., twist position or rotational position relative to a longitudinal axis along the forearm), the fourth string encoder 210d and the fifth string encoder 210e of the illustrated example (e.g., a double encoder) generates a fourth strain output 308 (e.g., a summation of an output of the fourth string encoder 210d and the fifth string encoder) based on a position (e.g., a taut condition) of the fourth string 230d and the fifth string 230e, and the sixth string encoder 210f and the seventh string encoder 210g of the illustrated example (e.g., a double encoder) generates a fifth strain output 310 (e.g., a summation of an output of the sixth string encoder 210f and the seventh string encoder 210g) based on a position (e.g., a taut condition) of the sixth string 230f and the seventh string 230g.

Each example strain outputs 302-310 is representative of movements of the arm 102a relative to an initial position (e.g., the arm 102a positioned against the side of the body 106 with palm against the body 106). The example strain outputs 302-310 are representative of, and/or can be used to, detect an amount of strain imparted to the arm 102a during movement as the shoulder 202 rotates relative to the body 106, the elbow 206 bends at the elbow joint, the hand bends at the wrist, the arm 102a rotates relative to the shoulder 202, the forearm twists relative to the elbow and/or the shoulder, and/or any other position of the arm 102a relative to the body 106. The other positions can include various positions (e.g., rotating the arm 102a outward, lifting the arm 102a above a user's head, rotating the arm 102a in a circle, etc.).

The example limb sensor 201 of FIG. 2B produces similar outputs. For example, the sensor assemblies 200 of FIG. 2A can generate strain outputs 302-310 and the limb sensor 201 of FIG. 2B can generate strain outputs 302-312. For example, the first rotary encoder 257a can generate the first strain output 302 of the first strain outputs 300, the second rotary encoder 257b can generate the second strain output 304 of the first strain outputs 300, the third rotary encoder 257c can generate the third strain output 306 of the first strain outputs 300, the fourth rotary encoder 257d can generate the fourth strain output 308 of the first strain outputs 300, the fifth rotary encoder 257e can generate the fifth strain output 310 of the first strain outputs 300, and the sixth rotary encoder 257f can generate a sixth strain output 312 of the first strain outputs 300. The strain outputs 302-312 can be voltage, a current and/or any other type of signal.

Figure 4A:
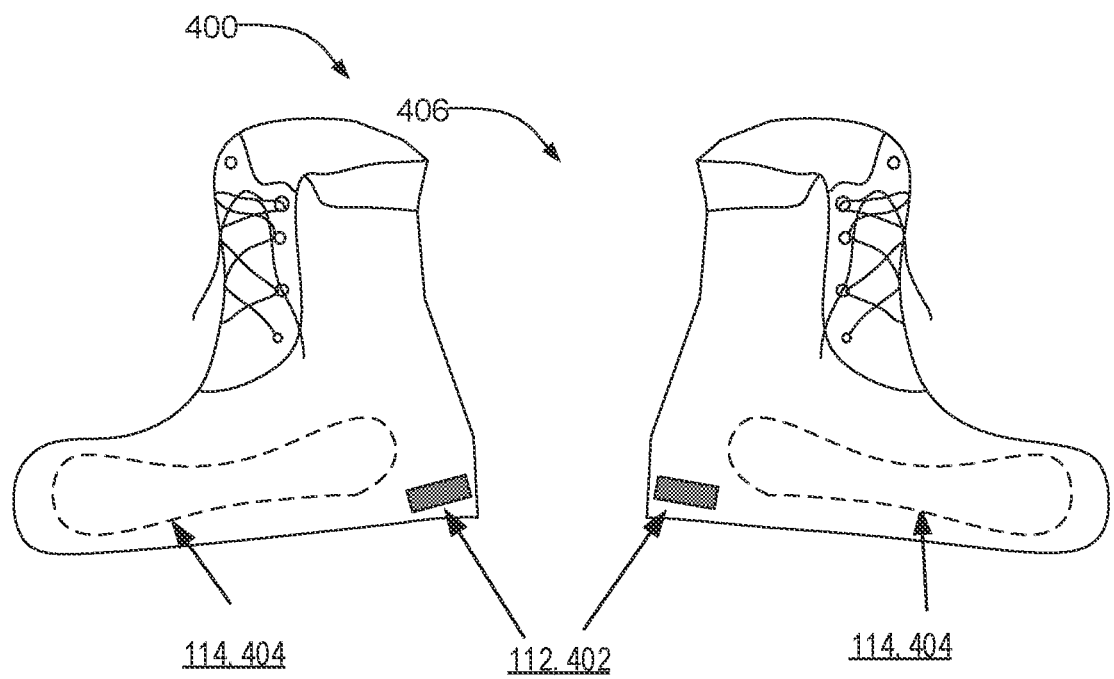
FIG. 4A is an example lower body sensor system of the example ergonomics improvement system of FIG. 1.

FIG. 4A is an example lower body sensor system 400 of the example ergonomics improvement system 100 of FIG. 1. The lower body sensor system 400 of the illustrated example implements the load sensor 112 and the position sensor 114 of FIG. 1. The load sensor 112 includes load cells 402 and the position sensor 114 includes pressure sensors 404 (e.g., a pressure pad, Stepscan® sensor, etc.). The load cells 402 and the pressure sensors 404 are located in (e.g., embedded in the soles of) a pair of shoes 406 that can be worn by the user 106a (FIG. 1). The load cells 402 measure a load or weight of the user 106a to determine an amount of weight that the user 106a is holding or lifting. The pressure sensors 404 of the illustrated example can detect and/or determine a stance (e.g., feet positioning) of the user 106a performing a physical task. For example, the pressure sensors 404 can detect and/or otherwise determine if a user is standing in a stable or bracing position (e.g., with one weight evenly distributed in the feet) or a non-stable or non-bracing position (e.g., a user standing with their weight all centered forward on the toes or all centered backwards on the heels) when performing a physical task. In some examples, the pressure sensors 404 can be used to determine weight distribution of the user (e.g., whether the weight distribution is centered). For example, a weight of the user 106a being offset toward the heels of the user 106a can indicate that the user 106a is off-balance and/or at risk of falling or being injured. In some examples, by determining a position of the arm 102a via the sensor assemblies 200, the position of each foot of the user 106a via the position sensor 114 and a load carried by the user 106a via the load sensor 112, the ergonomics improvement system 100 can determine if the user's stance is stable (e.g., or optimal) for carrying a detected load (e.g., the object 119 of FIG. 1).

Figure 4B:
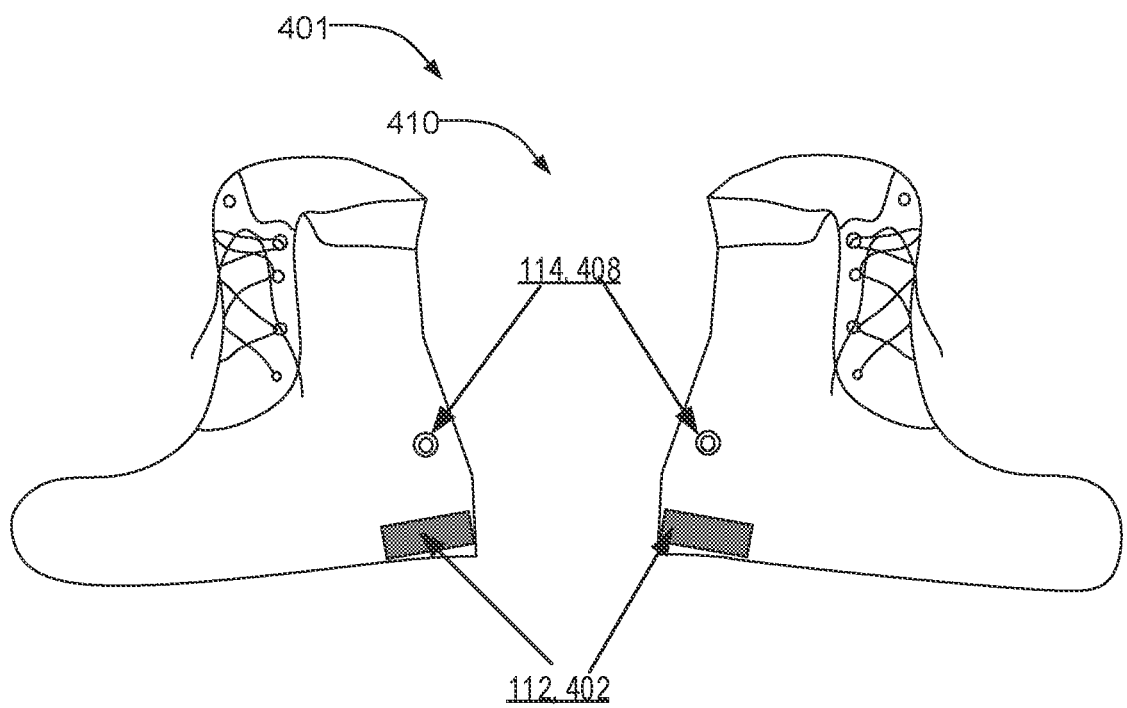
FIG. 4B is another example lower body sensor system disclosed herein that can be used to implement the example ergonomics improvement system of FIG. 1.

FIG. 4B is another example lower body sensor system 401 disclosed herein that can be used to implement the example ergonomics improvement system 100 of FIG. 1. The lower body sensor system 400 of the illustrated example implements the load sensor 112 and the position sensor 114 of FIG. 1. The load sensor 112 includes load cells 402 and the position sensor 114 includes Light Detection and Ranging (LiDAR) sensors 408 (e.g., a pressure pad, Stepscan® sensor, etc.). The load cells 402 and the LiDAR sensors 408 are incorporated (e.g., carried by, attached, or otherwise embedded) in a pair of shoes 410 to be worn by the user 106a. To detect position of the user's feet, the LiDAR sensors 408 emit pulsed waves into a surrounding environment. When the user stands with his feet together, the pulses bounce off the opposing shoe and return to the sensor. The sensor uses a time differential for each pulse to return to the sensor to calculate a distance it traveled. When a first foot is forward and/or rearward of the other foot, the pulsed waves project into the surrounding environment instead of an otherwise opposing shoe, indicating that the user's feet are spread apart. Thus, pulses emitted by the LiDAR sensors 408 can be used to determine if the user 106a is standing in a stable or bracing position (e.g., with one foot spaced apart and in front of their other foot) or a non-stable or non-bracing position (e.g., a user standing with their feet spaced apart, but the left foot substantially even with the right foot) when performing the physical tasks.

Figure 5B:
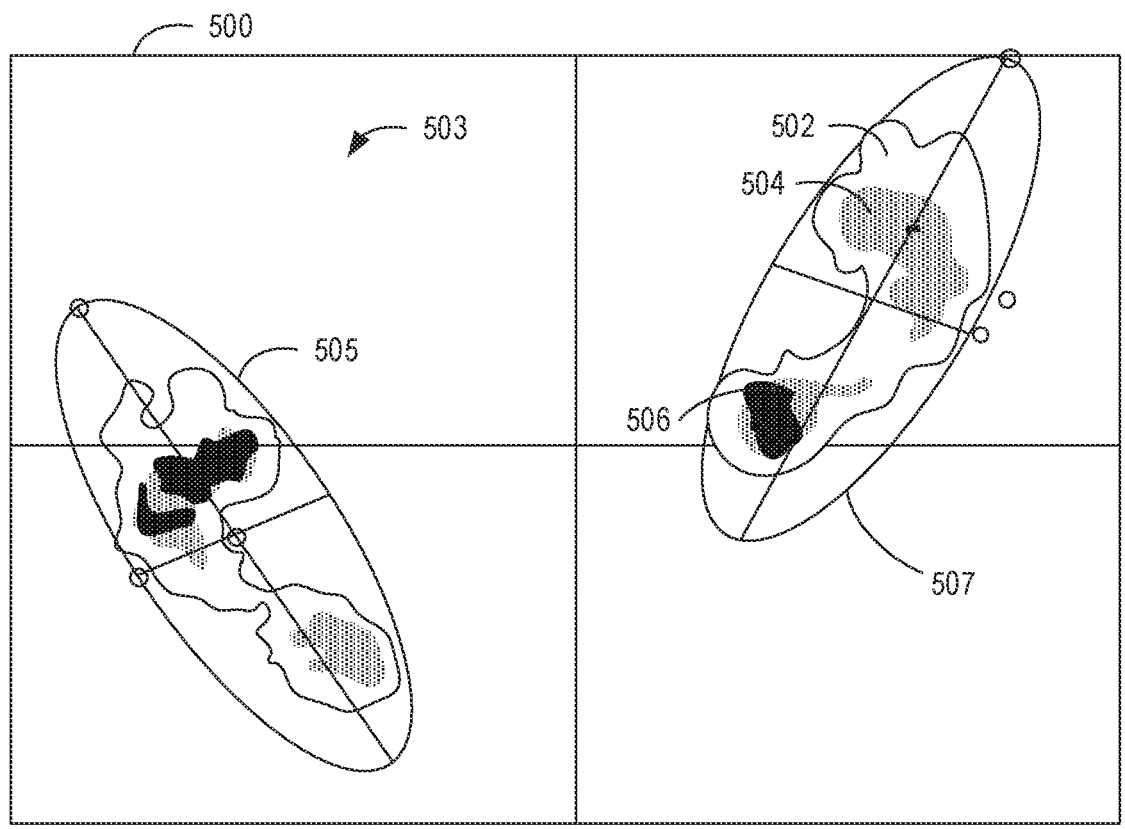

FIGS. 5A and 5B are schematic illustrations of example third outputs 500 of the example lower body sensor system 400 of FIG. 4A. FIG. 5A is illustrates a first one 501 of the third outputs 500 and FIG. 5B illustrates a second one 503 of the third outputs 500. For example, the first one 501 of the third outputs 500 is representative of the user 106a having his/her feet spaced apart, but a left foot 505 substantially even with a right foot 507. The second one 503 of the third outputs 500 of FIG. 5B is representative of the user 106a having the right foot 507 spaced apart and in front of the left foot 505. The pressure sensors 404 generate Stepscan® or pressure outputs, such as shown in FIGS. 5A and 5B. The third outputs 500 of the pressure sensors 404 can detect pressure distribution across the feet of the user 106a. For example, a white colored area 502 in FIGS. 5A and 5B indicates an area with low pressure, a grey colored area 504 in FIGS. 5A and 5B indicates medium pressure, and a black colored area 506 in FIGS. 5A and 5B indicates high pressure. In FIG. 5A the user has more pressure on his/her right foot 507 as indicated by more grey colored area 504 and more black colored area 506 as compared to the left foot 505 which has more white colored area 502. FIG. 5B illustrates the weight of the user 106a concentrated in the back heel of the right foot 507 and concentrated on a pad or middle area of the left foot 505.

Figure 6:
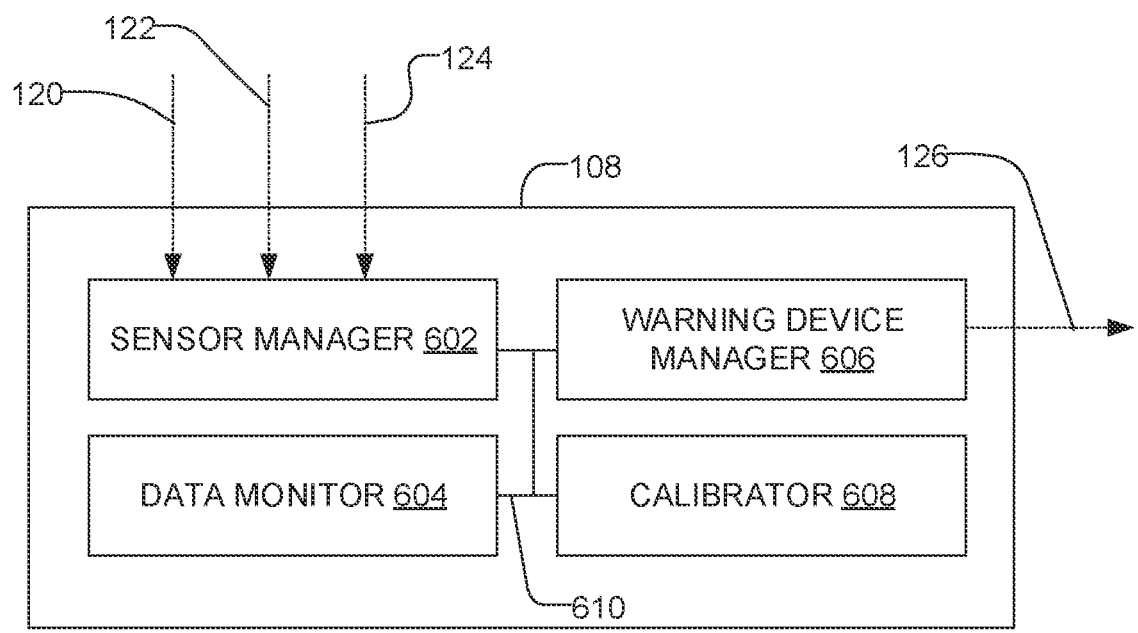
FIG. 6 is a block diagram of an example controller of the example ergonomics improvement system of FIG. 1.

FIG. 6 is a block diagram of the example controller 108 of the example ergonomics improvement system 100 of FIG. 1. The controller 108 includes a sensor manager 602, a data monitor 604, a warning device manager 606, and a calibrator 608. The sensor manager 602, the data monitor 604, the warning device manager 606 and the calibrator 608 are communicatively coupled via a bus 610.

The sensor manager 602 receives inputs from the limb sensor 110, the load sensor 112, or/and the position sensor 114. For example, the sensor manager 602 receives the limb sensor outputs 120, the load sensor outputs 122, and/or the position sensor outputs 124. For example, the sensor manager 602 receives the strain outputs 302-312, the outputs from the load cells 402, and the outputs from the pressure sensors 404 and/or the LiDAR sensors 408. The sensor manager 602 receives the outputs as currents, voltages, etc. In some examples, the sensor manager 602 can condition the signals for processing by the data monitor 604. In some examples, the sensor manager 602 converts the inputs to binary values (e.g., on/off), digital values, and/or an analog values. For example, the sensor manager 602 can convert the signals of the position sensor 114 to binary values.

For example, the sensor manager 602 can provide binary values "1" for respective ones of the strain outputs 302-310 of the string encoders 210a-g in response to the output signals not exceeding a threshold value (e.g., an electric current) associated with the respective ones of the string encoders 210a-g and can provide binary values "0" for respective ones of the strain outputs 302-310 of the string encoders 210a-g in response to the output signals exceeding a threshold value (e.g. an electric current) associated with the respective ones of the string encoders 210a-g. For example, the sensor manager 602 can provide a binary value "1" when the position sensor 114 provides signals representative of the user 106a being in the stable stance and a binary value "0" when the position sensor 114 provides signals representative of the user 106a being in a non-stable stance. In some examples, the sensor manager 602 can provide a binary value "1" in response to the load sensor 112 providing a signal representative of a weight that is greater than a threshold (e.g., 50 pounds) and a binary value "0" in response to the load sensor 112 providing a signal representative of a weight being less than the threshold.

The data monitor 604 stores and processes the signal(s) from the sensor manager 602. The data monitor 604 can compare signal(s) from the sensor manager 602 to a threshold. In some examples, the threshold can be obtained, retrieved, or otherwise accessed from memory by the data monitor 604. For example, the data monitor 604, via a comparator, can compare the signals from the sensor manager 602 to a table to determine if the user 106a is performing a non-ergonomic or improper activity based on the data provided by the limb sensor outputs 120, the load sensor outputs 122, and/or the position sensor outputs 124. For example, data monitor 604 can compare the signals from the sensor manager 602 to threshold values stored in a look-up table associated with respective thresholds for the respective ones of the limb sensor outputs 120, the load sensor outputs 122 and/or the position sensor output 124. For example, the data monitor 604 can compare a determined position of the limb 102 to a position threshold associated with a measured load carried by the user 106a provided by the load sensor 112 and a determined position of the right foot 507 relative to the left foot 505. The data monitor 604 can communicate a warning activation signal to the warning device manager 606 in response to determining that the detected position of the limb 102 exceeds a position threshold (e.g., from a look-up table) associated with or corresponding to the measured load from the load sensor 112 and/or the detected position of the right foot 507 relative to the left foot 505. For example, the strain outputs 302-310 of FIG. 3 can be indicative of non-ergonomic or improper movement or position of the limb 102 if a load carried by the user 106a exceeds a threshold load and/or a stance of the user 106a is a non-stable stance (e.g., a stance shown in FIG. 5A). In some instances, the strain outputs 302-310 of FIG. 3 can be indicative of non-ergonomic or improper movement or position of a limb 102 if a load carried by the user 106a does not exceed a threshold load and/or a stance of the user 106a is a stable stance (e.g., a stance shown in FIG. 5B).

For example, the look-up table can have a plurality of first threshold values corresponding to outputs from the string encoders 210a-g. Based on a comparison of the outputs from the string encoders 210a-g and the thresholds corresponding to the respective ones of the string encoders 210a-g stored in the lookup table, the weight provided by the load sensor 112, and the feet stance provided by the position sensor 114, the data monitor 604 determines if the user 106a is conducting activity (e.g., based on limb movement or position) that is ergonomically proper or ergonomically improper. If one or more signals or a combination of signals from the sensor manager 602 exceeds one or more thresholds or a combination of thresholds compared to the limb sensor outputs 120, the load sensor 122 and the position sensor outputs 124, then the warning device manager 606 triggers the warning signal 126 to trigger an alarm (e.g., indicative of a non-ergonomic activity or movement).

The warning device manager 606 can receive a signal from the data monitor 604 if the signal from the sensor manager 602 exceeds a threshold. The warning device manager 606 can send the warning signal 126 and/or alarm. Example alarms disclosed herein include, but are not limited to, visual alarms (e.g., a light), audio alarms (e.g., a speaker), haptic feedback (e.g., a vibration), a combination thereof and/or any other alarm(s). In some examples, the type of alarm(s) can be selected based on an environment (e.g., industrial or manufacturing environment) of the user. For example, where the environment can be noisy, busy, or where the tasks being performed should not be interrupted by abrupt or startling alarms, the type of alarm chosen (e.g., haptic feedback) can vary between the options discussed above and/or other types of alarms.

Figure 9:
FIG. 9 is an example diagram representative of example sensor calibration positions disclosed herein that can be used to implement the example calibration of FIG. 8.
Figure 9:
Figure 9:
Figure 9:
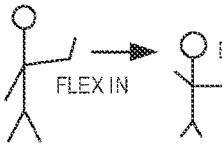
Figure 9:
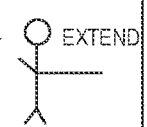
Figure 9:
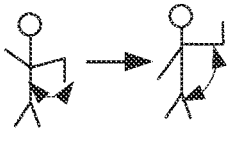
Figure 9:
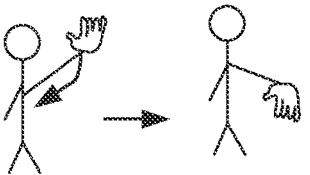
Figure 9:
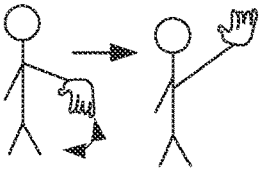
Figure 9:
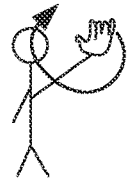

The calibrator 608 instructs users of motions to complete calibration such as those illustrated in FIG. 9. The calibrator 608 also stores movement data from various positions from the calibration and can process the movement data to be used as thresholds for the data monitor 604. The calibrator 608 sets a zero or reference value for the limb sensor 110, the load sensor 112 and the position sensor 114.

Alternatively, the controller 108 of the illustrated example can be configured to communicate the outputs (e.g., the outputs 120, 122, 124, 302-312, etc.) from the upper body sensor system 111a and/or the lower body sensor system 111b to a remote electronic device such as, for example, a server, a computer, a control room, a mobile device, a mobile phone, and/or any other computing device communicatively coupled to the controller 108 of the ergonomics improvement system 100. For example, the controller 108 and/or the sensor manager 602 can transmit or communicate one or more outputs provided by the sensors (e.g., the limb sensor 110, the load sensor 112, the position sensor 114, the string encoders 210a-g, the rotary encoders 257a-e, the load cells 402, the pressure sensors 404, the LiDAR sensors 408 and/or any other sensor(s)). The remote electronic device can be configured to model the movement of the user 106a (e.g., the arm 102a of the user 106a) based on the data provided by the controller 108. The remote electronic device can be configured to detect whether the model represents movements that can be indicative of movements that can be ergonomic or acceptable, or movements that can be non-ergonomic or not acceptable If the remote electronic device determines that the movements of the user 106a are acceptable, the remote electronic device does not communicate with the controller 108. If the remote electronic device determines that the movements of the user 106a are not acceptable, the remote electronic device communicate instructions to the controller 108 to cause the warning device manager 606 to initiate the warning signal 126 to active the warning device 116.

While an example manner of implementing the controller 108 of FIG. 1 is illustrated in FIG. 6, one or more of the elements, processes and/or devices illustrated in FIG. 6 may be combined, divided, re-arranged, omitted, eliminated and/or implemented in any other way. Further, the sensor manager 602, the data monitor 604, the warning device manager 606, and the calibrator 608. and/or, more generally, the example controller of FIG. 1 may be implemented by hardware, software, firmware and/or any combination of hardware, software and/or firmware. Thus, for example, any of the sensor manager 602, the data monitor 604, the warning device manager 606, and the calibrator 608. and/or, more generally, the example controller 108 of FIG. 1 could be implemented by one or more analog or digital circuit(s), logic circuits, programmable processor(s), programmable controller(s), graphics processing unit(s) (GPU(s)), digital signal processor(s) (DSP(s)), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the sensor manager 602, the data monitor 604, the warning device manager 606, and the calibrator 608. and/or, more generally, the example controller 108 of FIG. 1 is/are hereby expressly defined to include a non-transitory computer readable storage device or storage disk such as a memory, a digital versatile disk (DVD), a compact disk (CD), a Blu-ray disk, etc. including the software and/or firmware. Further still, the example controller 108 of FIG. 1 may include one or more elements, processes and/or devices in addition to, or instead of, those illustrated in FIG. 6, and/or may include more than one of any or all of the illustrated elements, processes, and devices. As used herein, the phrase "in communication," including variations thereof, encompasses direct communication and/or indirect communication through one or more intermediary components, and does not require direct physical (e.g., wired) communication and/or constant communication, but rather additionally includes selective communication at periodic intervals, scheduled intervals, aperiodic intervals, and/or one-time events.

Figure 7:
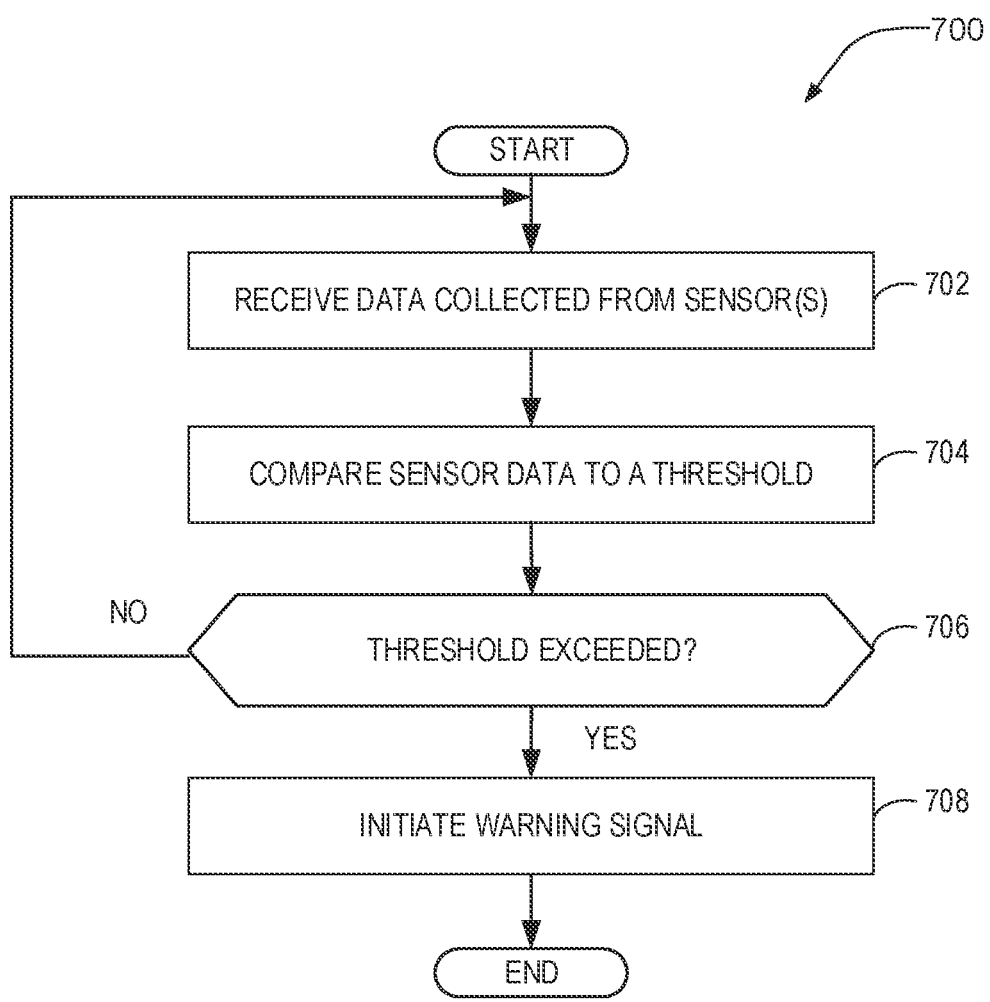
FIG. 7 is an example of a flowchart representative of an example method that can be performed by the example controller of FIG. 6 to analyze sensor data and activate an example warning device of the example ergonomics improvement system of FIG. 1.
Figure 8:
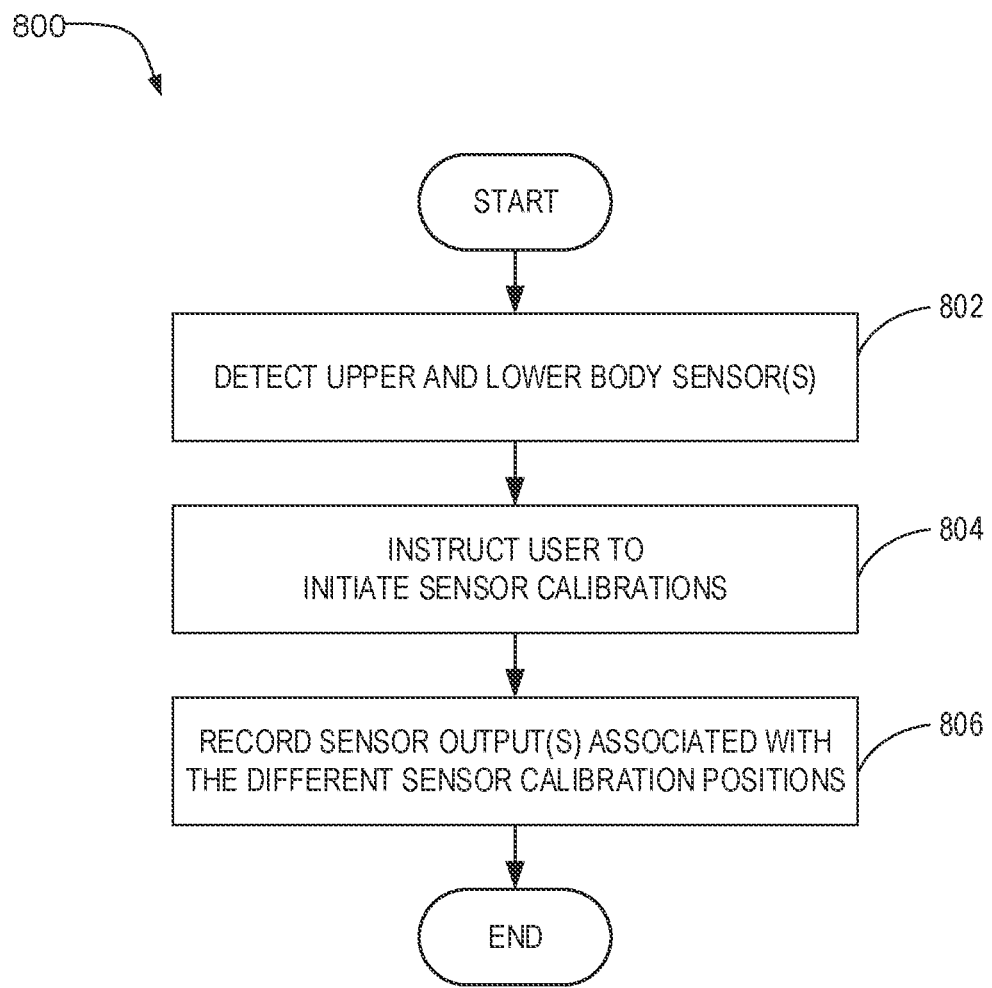
FIG. 8 is an example of a flowchart representative of an example method to calibrate example upper and lower body sensor systems of the example ergonomics improvement system of FIG. 1.
Figure 10:
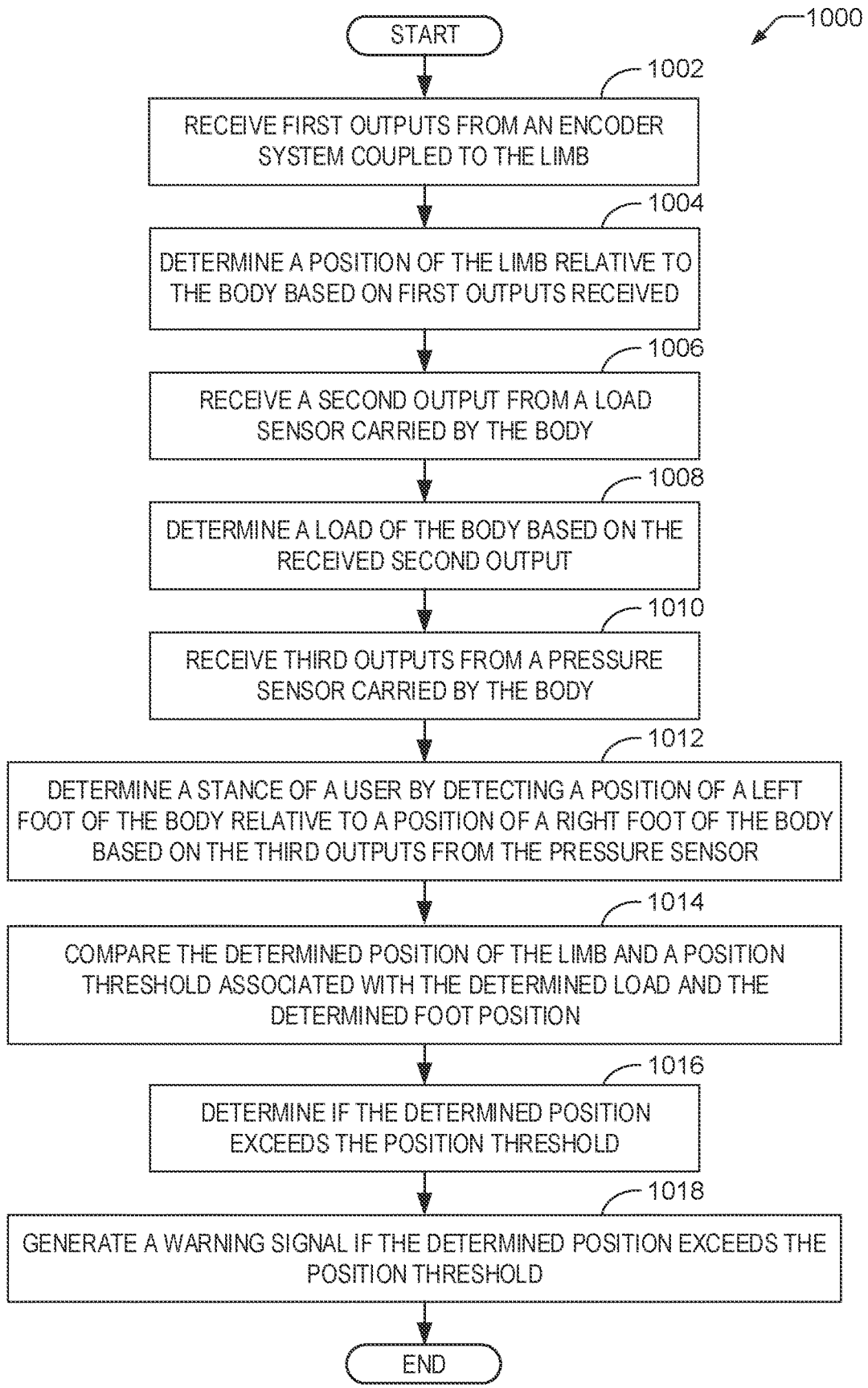
FIG. 10 is an example of a flowchart representative of an example method to implement the example ergonomics improvement system of FIG. 1.

Flowchart's representative of example hardware logic, machine readable instructions, hardware implemented state machines, and/or any combination thereof for implementing the ergonomics improvement system 100 of FIG. 1 is shown in FIG. 7, FIG. 8, and FIG. 10. The machine readable instructions may be one or more executable programs or portion(s) of an executable program for execution by a computer processor such as the processor 1112 shown in the example processor platform 1100 discussed below in connection with FIG. 1. The program may be embodied in software stored on a non-transitory computer readable storage medium such as a CD-ROM, a floppy disk, a hard drive, a DVD, a Blu-ray disk, or a memory associated with the processor 1112, but the entire program and/or parts thereof could alternatively be executed by a device other than the processor 1112 and/or embodied in firmware or dedicated hardware. Further, although the example program is described with reference to the flowchart illustrated in FIGS. 7, 8 and 10, many other methods of implementing the example ergonomics improvement system 100 may alternatively be used. For example, the order of execution of the blocks may be changed, and/or some of the blocks described may be changed, eliminated, or combined. Additionally, or alternatively, any or all of the blocks may be implemented by one or more hardware circuits (e.g., discrete and/or integrated analog and/or digital circuitry, an FPGA, an ASIC, a comparator, an operational-amplifier (op-amp), a logic circuit, etc.) structured to perform the corresponding operation without executing software or firmware.

The machine readable instructions described herein may be stored in one or more of a compressed format, an encrypted format, a fragmented format, a compiled format, an executable format, a packaged format, etc. Machine readable instructions as described herein may be stored as data (e.g., portions of instructions, code, representations of code, etc.) that may be utilized to create, manufacture, and/or produce machine executable instructions. For example, the machine readable instructions may be fragmented and stored on one or more storage devices and/or computing devices (e.g., servers). The machine readable instructions may require one or more of installation, modification, adaptation, updating, combining, supplementing, configuring, decryption, decompression, unpacking, distribution, reassignment, compilation, etc. to make them directly readable, interpretable, and/or executable by a computing device and/or other machine. For example, the machine readable instructions may be stored in multiple parts, which are individually compressed, encrypted, and stored on separate computing devices, wherein the parts when decrypted, decompressed, and combined form a set of executable instructions that implement a program such as that described herein.

In another example, the machine readable instructions may be stored in a state in which they may be read by a computer, but require addition of a library (e.g., a dynamic link library (DLL)), a software development kit (SDK), an application programming interface (API), etc. to execute the instructions on a particular computing device or other device. In another example, the machine readable instructions may need to be configured (e.g., settings stored, data input, network addresses recorded, etc.) before the machine readable instructions and/or the corresponding program(s) can be executed in whole or in part. Thus, the disclosed machine readable instructions and/or corresponding program(s) are intended to encompass such machine readable instructions and/or program(s) regardless of the particular format or state of the machine readable instructions and/or program(s) when stored or otherwise at rest or in transit.

The machine readable instructions described herein can be represented by any past, present, or future instruction language, scripting language, programming language, etc. For example, the machine readable instructions may be represented using any of the following languages: C, C++, Java, C#, Perl, Python, JavaScript, HyperText Markup Language (HTML), Structured Query Language (SQL), Swift, etc.

As mentioned above, the example processes of FIGS. 7, 8, and 10 may be implemented using executable instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media.

"Including" and "comprising" (and all forms and tenses thereof) are used herein to be open ended terms. Thus, whenever a claim employs any form of "include" or "comprise" (e.g., comprises, includes, comprising, including, having, etc.) as a preamble or within a claim recitation of any kind, it is to be understood that additional elements, terms, etc. may be present without falling outside the scope of the corresponding claim or recitation.

As used herein, when the phrase "at least" is used as the transition term in, for example, a preamble of a claim, it is open-ended in the same manner as the term "comprising" and "including" are open ended. The term "and/or" when used, for example, in a form such as A, B, and/or C refers to any combination or subset of A, B, C such as (1) A alone, (2) B alone, (3) C alone, (4) A with B, (5) A with C, (6) B with C, and (7) A with B and with C. As used herein in the context of describing structures, components, items, objects and/or things, the phrase "at least one of A and B" is intended to refer to implementations including any of (1) at least one A, (2) at least one B, and (3) at least one A and at least one B. Similarly, as used herein in the context of describing structures, components, items, objects and/or things, the phrase "at least one of A or B" is intended to refer to implementations including any of (1) at least one A, (2) at least one B, and (3) at least one A and at least one B. As used herein in the context of describing the performance or execution of processes, instructions, actions, activities and/or steps, the phrase "at least one of A and B" is intended to refer to implementations including any of (1) at least one A, (2) at least one B, and (3) at least one A and at least one B. Similarly, as used herein in the context of describing the performance or execution of processes, instructions, actions, activities and/or steps, the phrase "at least one of A or B" is intended to refer to implementations including any of (1) at least one A, (2) at least one B, and (3) at least one A and at least one B.

As used herein, singular references (e.g., "a", "an", "first", "second", etc.) do not exclude a plurality. The term "a" or "an" entity, as used herein, refers to one or more of that entity. The terms "a" (or "an"), "one or more", and "at least one" can be used interchangeably herein. Furthermore, although individually listed, a plurality of means, elements or method actions may be implemented by, e.g., a single unit or processor. Additionally, although individual features may be included in different examples or claims, these may possibly be combined, and the inclusion in different examples or claims does not imply that a combination of features is not feasible and/or advantageous.

The method 700 of FIG. 7 is an example method for implementing the ergonomics improvement system 100 of FIG. 1. The method 700 begins at block 702, with the sensor manager 602 receiving data collected from sensor(s). The sensor(s) can include the limb sensor 110, the load sensor 112, the position sensor 114, the string encoders 210a-g, the rotary encoders 257a-f, the load cells 402, the pressure sensor 404, the LiDAR sensors 408 and/or any other sensor(s).

At block 704, the data monitor 604 compares data (e.g., signals(s)) from the sensor manager 602 data to a threshold. The threshold can be obtained from a lookup table that can be stored in a database or memory of the controller 108.

At block 706, the data monitor 604 determines whether the threshold at block 704 is exceeded. If the data monitor 604 determines that the threshold is exceeded at block 706, then the process continues to block 708. At block 708, the warning device manager 606 initiates a warning signal (e.g., the warning signal 126) to activate the alarm and/or warning device 116. If the data monitor 604 determines at block 706 that the threshold is not exceeded, then the process returns to block 702.

Referring to FIG. 8, the method 800 is an example method to calibrate the upper body sensor system 111a and the lower body sensor system 111b of the example ergonomics improvement system 100 of FIG. 1. For example, calibration can be implemented using the calibrator 608. For example, calibration of the example ergonomics improvement system 100 of FIG. 1 can occur when the system is initially turned on and/or at any other time when the system is in use. In some examples, calibration can be automatically set to occur at pre-defined intervals or at certain events such as when the controller 108 detects outlier values outputted by one or more sensors of the ergonomics improvement system of FIG. 1.

At block 802, the example ergonomics improvement system 100 of FIG. 1 can detect the upper body sensor system 111a (e.g., the string encoders 210a-g, the rotary encoders 257a-e) and the lower body sensor system 111b (e.g., the load cells 402, the pressure sensor 404, the LiDAR sensor 408, etc.) via the sensor manager 602. At block 804, the example calibrator 608 instructs the user 106a to initiate sensor calibrations. Example sensor calibration positions are disclosed herein and are illustrated and discussed in FIG. 9.

At block 806, the example calibrator 608 records sensor output(s) associated with the different sensor calibrations. For example, the calibrated values for each of the sensors (e.g., the limb sensor 110, the load sensor 112, and/or the position sensor 114) are zero values or reference values.

FIG. 9 is an example diagram representative of example calibration positions 900 disclosed herein that can be used to implement the example method 800 of FIG. 8. The sensor calibration positions can be instructed to the user 106a using a user interface that can include, for example, a display, a speaker, a combination thereof, and/or any other communication device carried by the controller 108. The example calibration positions 900 can be used to calibrate one or more of the string encoders 210a-g and/or the rotary encoders 257a-e after the sensors are carried or coupled to the user 106a. For example, each of the string encoders 210a-f and/or each of the rotary encoders 257a-e can be calibrated using the example calibration positions 900 of FIG. 9. For example, the calibration positions 900 include three sets of calibration positions (i.e., position 1, position 2, position 3) for each of the shoulder 204, the elbow 206 and the wrist 208. However, the calibration positions are not limited to the positions shown in FIG. 9 and can include one or more other positions that are not shown in FIG. 9.

In position 1 of a shoulder calibration 902, the user 106a is instructed to move their arms (i.e., the arm 102a) in a forward position (e.g., a fully forward extended position in a direction in front of the user 106a) and rearward position (e.g., a fully rearward extended position in a direction behind the user 106a). The controller 108 records outputs of the sensors (e.g., the string encoders 210a-b, the rotary encoders 257a-b and/or the fifth rotary encoder 257e) when the arm 102a moves to the forward position and the rearward position.

In position 2 of a shoulder calibration 904, the user 106a is instructed to move their arms in an upward position (e.g., a fully raised position above the user's head) and downward position (e.g., a fully extended position on the side of the user's body). The controller 108 records outputs of the sensors (e.g., the string encoders 210a-b, the rotary encoders 257a-b and/or the fifth rotary encoder 257e) when the arm 102a moves to the upward position and the downward position.

In position 3 of a shoulder calibration 906, the user 106a is instructed to extend their arms outwardly and sideways (e.g., a wingspan formation) and rotate/twist their arms in a circular motion between a first rotational position (e.g., twist or rotate in a first rotational position) and a second rotational position (e.g., twist or rotate in a second rotational direction opposite the first direction). The controller 108 records outputs of the sensors (e.g., the string encoders 210a-b, the rotary encoders 257a-b and/or the fifth rotary encoder 257e) when the arm 102a moves to the first rotational position and the first rotational position.

In position 1 of an elbow calibration 908, the user 106a is instructed to move their arms sideways and to move their arms to a curled position (e.g., fully curled position where the hand is proximate the shoulder 204) and an extended position (e.g., a fully extended position). The controller 108 records outputs of the sensors (e.g., the third string encoder 210c, the rotary encoders 257c, and/or 257e-f) associated with the elbow 206 when the arm 102a moves to the curled position and the extended position.

In position 2 of an elbow calibration 910, the user 106a is instructed to bend their elbows and move their elbows while in the bent position to a bent upward position and a bent downward position. The controller 108 records outputs of the sensors (e.g., the third string encoder 210c, the rotary encoders 257c, and/or 257e-f) when the arm 102a moves to the bent upward position and the bent downward position.

In position 3 of the elbow calibration 912, the user 106a is instructed to rotate their arms with the elbow bent between a first rotational position and a second rotational position opposite the first rotational position. The controller 108 records outputs of the sensors (e.g., the third string encoder 210c, the rotary encoders 257c, and/or 257e-f) when the arm 102a, with the bent elbow 206, moves to the first rotational position and the second rotational position.

In position 1 of a wrist/hand calibration 914, the user 106a is instructed to move or bend their hand about the wrist to an upward position (e.g., fully upward position) and a downward position (e.g., a fully downward position). The controller 108 records outputs of the sensors (e.g., the string encoder 210d-g, the rotary encoders 257d and/or 257f) when the hand moves to the first rotational position and the second rotational position.

In position 2 of a wrist/hand calibration 916, the user 106a is instructed to move their hand sideways about the wrist to a first side position (e.g., fully right side position) and a second side position (e.g., a fully left side position). The controller 108 records outputs of the sensors (e.g., the string encoder 210d-g, the rotary encoders 257d and/or 257f) when the hand moves to the first side position and the second side position.

In position 3 of a wrist/hand calibration 918, the user 106a is instructed to twist their hand sideways about the wrist to a first rotational position (e.g., a fully rotational position in a first rotational direction) and a second rotational position (e.g., a fully rotational position in a second rotational direction). The controller 108 records outputs of the sensors (e.g., the string encoder 210d-g, the rotary encoders 257d and/or 257f) when the hand moves to the first rotational position and the second rotational position.

FIG. 10 is an example of a flowchart representative of an example method 1000 to implement the example ergonomics improvement system 100 of FIG. 1. The method 1000 of FIG. 10 is an example method for implementing the ergonomics improvement system 100 of FIG. 1.

The method 1000 begins at block 1002, with the sensor manager 602, receiving first outputs from an encoder system (e.g., limb sensor 110) coupled to the limb 102. The limb sensor 110 is to track and/or detect movement of the limb 102 and/or the joint. At block 1004, the sensor manager 602 determines a position of the limb 102 relative to the body 106 based on the first outputs received from a position sensor 114.

At block 1006, the sensor manager 602 receives a second output from a load sensor 112 carried by the body 106. The load sensor 112 is to detect and/or measure a load carried by the body 106. At block 1008, the sensor manager 602 determines a load of the body 106 based on the received second output.

At block 1010, the sensor manager 602 receives third outputs from a pressure sensor (e.g., the load sensor 112) carried by the body 106. At block 1012, a sensor manager 602 determines a stance of a user by detecting a position of a left foot 505 of the body 106 relative to a position of a right foot 507 of the body 106 based on the third outputs from the pressure sensor (e.g., the load sensor 112). The position sensor 114 is to detect and/or otherwise determine a stance (e.g., feet positioning) of a user.

At block 1014, the data monitor 604 compares the determined position of the limb 102 and a position threshold associated with the determined load and the determined foot position. At block 1016, the data monitor 604, determines if the determined position exceeds the position threshold. The data monitor 604 can compare signal(s) from the sensor manager 602 to the position threshold.

At block 1018, the warning device manager 606, generates a warning signal if the determined position exceeds the position threshold. The warning device manager 606 can receive a signal from the data monitor 604 if the signal from the sensor manager 602 exceeds the position threshold. The warning device manager 606 can send the warning signal 126 and/or alarm. Example alarms disclosed herein include, but are not limited to, visual alarms (e.g., a light), audio alarms (e.g., a speaker), haptic feedback (e.g., a vibration), a combination thereof and/or any other alarm(s).

Figure 11:
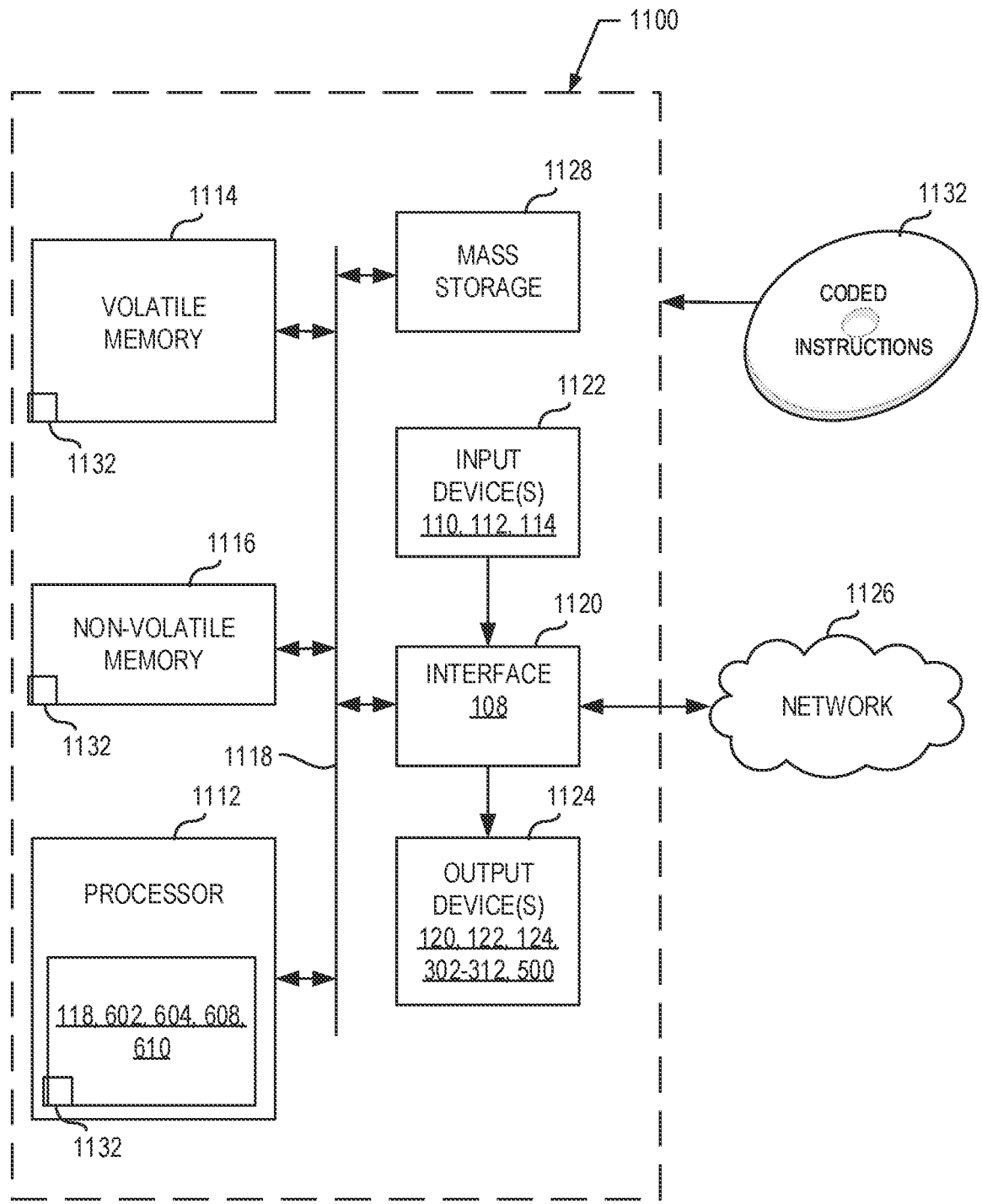
FIG. 11 is a block diagram of an example processing platform structured to execute instructions of FIGS. 7 and 8 to implement an example controller of example ergonomics improvement systems disclosed herein.

FIG. 11 is a block diagram of an example processing platform structured to execute instructions of FIGS. 7 and 8 to implement an example controller of example ergonomics improvement systems disclosed herein.

FIG. 11 is a block diagram of an example processor platform 1100 structured to execute the instructions of FIGS. 7, 8 and 10 to implement the ergonomics improvement system 100 of FIG. 1. The processor platform 1100 can be, for example, a server, a personal computer, a workstation, a self-learning machine (e.g., a neural network), a mobile device (e.g., a cell phone, a smart phone, a tablet such as an iPad™, a headset or other wearable device, or any other type of computing device.

The processor platform 1100 of the illustrated example includes a processor 1112. The processor 1112 of the illustrated example is hardware. For example, the processor 1112 can be implemented by one or more integrated circuits, logic circuits, microprocessors, GPUs, DSPs, or controllers from any desired family or manufacturer. The hardware processor may be a semiconductor based (e.g., silicon based) device. In this example, the processor implements the sensor manager 602, the data monitor 604, the warning device manager 606 and the calibrator 608.

The processor 1112 of the illustrated example includes a local memory 1113 (e.g., a cache). The processor 1112 of the illustrated example is in communication with a main memory including a volatile memory 1114 and a non-volatile memory 1116 via a bus 1118. The volatile memory 1114 may be implemented by Synchronous Dynamic Random Access Memory (SDRAM), Dynamic Random Access Memory (DRAM), RAMBUS® Dynamic Random Access Memory (RDRAM®) and/or any other type of random access memory device. The non-volatile memory 1116 may be implemented by flash memory and/or any other desired type of memory device. Access to the main memory 1114, 1116 is controlled by a memory controller.

The processor platform 1100 of the illustrated example also includes an interface circuit 1120. The interface circuit 1120 may be implemented by any type of interface standard, such as an Ethernet interface, a universal serial bus (USB), a Bluetooth® interface, a near field communication (NFC) interface, and/or a PCI express interface.

In the illustrated example, one or more input devices 1122 are connected to the interface circuit 1120. The input device(s) 1122 permit(s) a user to enter data and/or commands into the processor 1112. The input device(s) can be implemented by, for example, an audio sensor, a microphone, a camera (still or video), a keyboard, a button, a mouse, a touchscreen, and/or a voice recognition system.

One or more output devices 1124 are also connected to the interface circuit 1120 of the illustrated example. The output devices 1124 can be implemented, for example, by display devices (e.g., a light emitting diode (LED), an organic light emitting diode (OLED), a liquid crystal display (LCD), a cathode ray tube display (CRT), an in-place switching (IPS) display, a touchscreen, etc.), and/or speaker. The interface circuit 1120 of the illustrated example, thus, typically includes a graphics driver card, a graphics driver chip and/or a graphics driver processor.

The interface circuit 1120 of the illustrated example also includes a communication device such as a transmitter, a receiver, a transceiver, a modem, a residential gateway, a wireless access point, and/or a network interface to facilitate exchange of data with external machines (e.g., computing devices of any kind) via a network 1126. The communication can be via, for example, an Ethernet connection, a digital subscriber line (DSL) connection, a telephone line connection, a coaxial cable system, a satellite system, a line-of-site wireless system, a cellular telephone system, etc.

The processor platform 1100 of the illustrated example also includes one or more mass storage devices 1128 for storing software and/or data. Examples of such mass storage devices 1128 include floppy disk drives, hard drive disks, compact disk drives, Blu-ray disk drives, redundant array of independent disks (RAID) systems, and digital versatile disk (DVD) drives.

The machine executable instructions 1132 of FIG. 7 and FIG. 8 may be stored in the mass storage device 1128, in the volatile memory 1114, in the non-volatile memory 1116, and/or on a removable non-transitory computer readable storage medium such as a CD or DVD.

The foregoing examples of the ergonomics improvement systems can be wearable devices. Although each example ergonomics improvement systems disclosed above have certain features, it should be understood that it is not necessary for a particular feature of one example to be used exclusively with that example. Instead, any of the features described above and/or depicted in the drawings can be combined with any of the examples, in addition to or in substitution for any of the other features of those examples. One example's features are not mutually exclusive to another example's features. Instead, the scope of this disclosure encompasses any combination of any of the features.

Further, the disclosure comprises examples according to the following clauses:

1. A wearable ergonomics improvement system to track movement of human limbs including an encoder system to couple to a limb of a body, the encoder system to generate first outputs in response to movement of the limb relative to the body to determine a position of the limb relative to the body, a load sensor to generate a second output representative of a load carried by the body, and a position sensor to generate a third output representative of a position of a right foot of the body relative to a position of a left foot of the body.

2. The system of any preceding clause, wherein the encoder system includes: a first encoder assembly to generate first ones of the first outputs in response to movement of a shoulder to determine a first position of a shoulder relative to the body, a second encoder assembly to generate second ones of the first outputs in response to movement of an elbow to detect a second position of an elbow relative to the body, and a third encoder assembly to generate third ones of the first outputs in response to movement of hand to detect a position of the hand relative to the body.

3. The system of any preceding clause, wherein the first encoder assembly is to be coupled adjacent to the shoulder, the second encoder assembly is to be coupled adjacent the elbow, and the third encoder assembly is to be coupled adjacent the hand.

4. The system of any preceding clause, wherein the first ones of the first outputs, the second ones of the first outputs and the third ones of the first outputs collectively determine a position of an arm relative to the body.

5. The system of any preceding clause, wherein the first encoder assembly is a first string encoder assembly including: a first string encoder, a first anchor, a first string having a first end coupled to the first string encoder and a second end attached to the body via the first anchor, the first string to extend at least partially across a shoulder joint of the body, a second string encoder, a second anchor, and a second string having a first end coupled to the second string encoder and a second end coupled to the body via the second anchor, the second string to extend across at least partially across the shoulder joint of the body, and the second string to cross the first string.

6. The system of any preceding clause, wherein the second encoder assembly is a second string encoder assembly including: a third string encoder, a third anchor, and a third string having a first end coupled to the third string encoder and a second end attached to the body via the third anchor, the third string to extend at least partially across an elbow joint of the body.

7. The system of any preceding clause, wherein the third encoder assembly is a third string encoder assembly including: a fourth string encoder, a fourth anchor, a fourth string having a first end coupled to the fourth string encoder and a second end attached to the body via the fourth anchor, the fourth string to extend at least partially across a wrist joint the body, a fifth string encoder, a fifth anchor, and a fifth string having a first end coupled to the fifth string encoder and a second end coupled to the body via the fifth anchor, the fifth string to extend at least partially across the wrist joint of the body, and the fifth string to cross the fourth string.

8. The system of any preceding clause, wherein the first encoder assembly includes a first rotational encoder assembly including: a first rotational encoder to couple adjacent a first portion of a shoulder joint of the body, the first rotational encoder to generate first ones of the first outputs in response to movement of a shoulder, and a second rotational encoder to couple adjacent a second portion of the shoulder joint of the body different from the first portion, the second rotational encoder to generate second ones of the first outputs in response to movement of the shoulder.

9. The system of any preceding clause, wherein the second encoder assembly includes a third rotational encoder to couple adjacent an elbow joint of the body, the third rotational encoder to generate third ones of the first outputs in response to movement of the elbow joint.

10. The system of any preceding clause, wherein the third encoder assembly includes a fourth rotational encoder to couple adjacent the wrist joint of the body, the fourth rotational encoder to generate fourth ones of the first outputs in response to movement of the wrist joint.

11. The system of any preceding clause, further including: a fifth encoder assembly to couple adjacent a forearm of the body, the fifth encoder assembly to generate fifth ones of the first outputs in response to movement of a forearm to detect at least one of a position or rotation of the forearm, and a fifth encoder assembly to couple adjacent to an upper arm portion of the body between the elbow and the shoulder, the fifth encoder to generate fifth ones of the first outputs in response to movement of an upper arm to detect at least one of a position or rotation of the upper arm.

12. The system of any preceding clause, wherein the load sensor is a load cell positioned in footwear that is to be worn by a user.

13. The system of any preceding clause, wherein the position sensor includes a LiDAR sensor to be carried by the footwear to be worn by the user.

14. The system of any preceding clause, wherein the position sensor includes a pressure sensor to be carried by the footwear to be worn by the user.

15. The system of any preceding clause, further including at least one of a battery or an energy generating system.

16. A system to track movement of a limb of a body, the system including: an upper body sensor system structured to be attached to the limb of the body, the upper body sensor system including encoders that generate first outputs in response to movements of the limb, a lower body sensor system, the lower body sensor system to generate a second outputs representative of a load carried by the body and third outputs representative of a positioning of a right foot of the body relative to the left foot of the body, and a processor to: determine a position of the limb relative to the body based on the first outputs, determine a measured load based on the second outputs, determine a position of the right foot of the body relative to the left foot of the body based on the third outputs, compare the determined position of the limb to a position threshold associated with the measured load and the detected position of the right foot relative to the left foot, and generate a warning signal in response to determining that the detected position exceeds the position threshold associated with the measured load and the detected position of the right foot relative to the left foot.

17. The system of any preceding clause, wherein the lower body sensor includes a load cell.

18. The system of any preceding clause, wherein the lower body sensor includes at least one of a pressure sensor or a LiDAR sensor.

19. A method for tracking movement of a limb of a body, the method comprising: receiving first outputs from an encoder system coupled to the limb, determining a position of the limb relative to the body based on first outputs received, receiving a second output from a load sensor carried by the body, determining a load of the body based on the received second output, receiving third outputs from a pressure sensor carried by the body, determining a foot position by detecting a position of a left foot of the body relative to a position of a right foot of the body based on the third outputs from the pressure sensor, comparing the determined position of the limb and a position threshold associated with the determined load and the determined foot position, determining if the determined position exceeds the position threshold, and generating a warning signal if the determined position exceeds the position threshold 20. The system of any preceding clause, wherein the generating of the warning signal includes generating at least one of a sound signal, a haptic signal, or a light signal.

Although certain example methods, apparatus and articles of manufacture have been described herein, the scope of coverage of this disclosure is not limited thereto. On the contrary, this disclosure covers all methods, apparatus and articles of manufacture fairly falling within the scope of the claims.

We claim:

1. A wearable ergonomics improvement system comprising:
    an encoder system to couple to a limb of a body, the encoder system to generate first outputs in response to movement of the limb relative to the body to determine a position of the limb relative to the body;
    a load sensor to generate a second output representative of a load carried by the body;
    a position sensor to generate a third output representative of a position of a right foot of the body relative to a position of a left foot of the body; and
    processor circuitry to detect whether the position of the limb exceeds a position threshold associated with the load and the foot position of the right foot relative to the left foot.

2. The system of claim 1, wherein the encoder system includes:
    a first encoder assembly to generate first ones of the first outputs in response to movement of a shoulder to determine a first position of the shoulder relative to the body;
    a second encoder assembly to generate second ones of the first outputs in response to movement of an elbow to detect a second position of the elbow relative to the body; and
    a third encoder assembly to generate third ones of the first outputs in response to movement of a hand to detect a position of the hand relative to the body.

3. The system of claim 2, wherein the first encoder assembly is to be coupled adjacent to the shoulder, the second encoder assembly is to be coupled adjacent the elbow, and the third encoder assembly is to be coupled adjacent the hand.

4. The system of claim 2, wherein the first ones of the first outputs, the second ones of the first outputs and the third ones of the first outputs collectively determine a position of an arm relative to the body.

5. A wearable ergonomics improvement system comprising:
    an encoder system to couple to a limb of a body, the encoder system to generate first outputs in response to movement of the limb relative to the body to determine a position of the limb relative to the body, the encoder system including:
        a first encoder assembly to generate first ones of the first outputs in response to movement of a shoulder to determine a first position of the shoulder relative to the body, wherein the first encoder assembly is a first string encoder assembly including:

a first string encoder;
a first anchor;
a first string having a first end coupled to the first string encoder and a second end attached to the body via the first anchor, the first string to extend at least partially across a shoulder joint of the body;
a second string encoder;
a second anchor; and
a second string having a first end coupled to the second string encoder and a second end coupled to the body via the second anchor, the second string to extend across at least partially across the shoulder joint of the body, and the second string to cross the first string;
a second encoder assembly to generate second ones of the first outputs in response to movement of an elbow to detect a second position of the elbow relative to the body; and
a third encoder assembly to generate third ones of the first outputs in response to movement of a hand to detect a position of the hand relative to the body;
a load sensor to generate a second output representative of a load carried by the body; and
a position sensor to generate a third output representative of a position of a right foot of the body relative to a position of a left foot of the body.

6. The system of claim 5, wherein the second encoder assembly is a second string encoder assembly including:
a third string encoder;
a third anchor; and
a third string having a first end coupled to the third string encoder and a second end attached to the body via the third anchor, the third string to extend at least partially across an elbow joint of the body.

7. The system of claim 5, wherein the third encoder assembly is a third string encoder assembly including:
a fourth string encoder;
a fourth anchor;
a fourth string having a first end coupled to the fourth string encoder and a second end attached to the body via the fourth anchor, the fourth string to extend at least partially across a wrist joint the body;
a fifth string encoder;
a fifth anchor; and
a fifth string having a first end coupled to the fifth string encoder and a second end coupled to the body via the fifth anchor, the fifth string to extend at least partially across the wrist joint of the body, and the fifth string to cross the fourth string.

8. The system of claim 2, wherein the first encoder assembly includes a first rotational encoder assembly including:
a first rotational encoder to couple adjacent a first portion of a shoulder joint of the body, the first rotational encoder to generate first ones of the first outputs in response to movement of the shoulder; and
a second rotational encoder to couple adjacent a second portion of the shoulder joint of the body different from the first portion, the second rotational encoder to generate second ones of the first outputs in response to movement of the shoulder.

9. The system of claim 8, wherein the second encoder assembly includes a third rotational encoder to couple adjacent an elbow joint of the body, the third rotational encoder to generate third ones of the first outputs in response to movement of the elbow joint.

10. The system of claim 9, wherein the third encoder assembly includes a fourth rotational encoder to couple adjacent a wrist joint of the body, the fourth rotational encoder to generate fourth ones of the first outputs in response to movement of the wrist joint.

11. A wearable ergonomics improvement system comprising:
an encoder system to couple to a limb of a body, the encoder system to generate first outputs in response to movement of the limb relative to the body to determine a position of the limb relative to the body, the encoder system including:
a first encoder assembly to generate first ones of the first outputs in response to movement of a shoulder to determine a first position of the shoulder relative to the body, the first encoder assembly including:
a first rotational encoder assembly having a first rotational encoder to couple adjacent a first portion of a shoulder joint of the body, the first rotational encoder to generate first ones of the first outputs in response to movement of the shoulder;
a second rotational encoder to couple adjacent a second portion of the shoulder joint of the body different from the first portion, the second rotational encoder to generate second ones of the first outputs in response to movement of the shoulder;
a second encoder assembly to generate second ones of the first outputs in response to movement of an elbow to detect a second position of the elbow relative to the body, the second encoder assembly including:
a third rotational encoder to couple adjacent an elbow joint of the body, the third rotational encoder to generate third ones of the first outputs in response to movement of the elbow joint;
a third encoder assembly to generate third ones of the first outputs in response to movement of a hand to detect a position of the hand relative to the body, the third encoder assembly including:
a fourth rotational encoder to couple adjacent a wrist joint of the body, the fourth rotational encoder to generate fourth ones of the first outputs in response to movement of the wrist joint;
a fourth encoder assembly to couple adjacent a forearm of the body, the fourth encoder assembly to generate fourth ones of the first outputs in response to movement of the forearm to detect at least one of a position or rotation of the forearm; and
a fifth encoder assembly to couple adjacent to an upper arm portion of the body between the elbow and the shoulder, the fifth encoder assembly to generate fifth ones of the first outputs in response to movement of the upper arm to detect at least one of a position or rotation of the upper arm;
a load sensor to generate a second output representative of a load carried by the body; and
a position sensor to generate a third output representative of a position of a right foot of the body relative to a position of a left foot of the body.

12. The system of claim 1, wherein the load sensor is a load cell positioned in footwear that is to be worn by a user.

13. The system of claim 1, wherein the position sensor includes at least one of a LiDAR sensor to be carried by footwear to be worn by a user.

14. The system of claim 1, wherein the position sensor includes a pressure sensor to be carried by footwear to be worn by a user.

15. The system of claim 1, further including at least one of a battery or an energy generating system.

16. A system to track movement of a limb of a body, the system including:
an upper body sensor system structured to be attached to the limb of the body, the upper body sensor system including encoders that generate first outputs in response to movements of the limb;
a lower body sensor system, the lower body sensor system to generate a second outputs representative of a load carried by the body and third outputs representative of a positioning of a right foot of the body relative to a left foot of the body; and
a processor to:
determine a position of the limb relative to the body based on the first outputs;
determine a measured load based on the second outputs;
determine a position of the right foot of the body relative to the left foot of the body based on the third outputs;
compare the determined position of the limb to a position threshold associated with the measured load and the determined position of the right foot relative to the left foot; and
generate a warning signal in response to determining that a detected position exceeds the position threshold associated with the measured load and the detected position of the right foot relative to the left foot.

17. The system of claim 16, wherein the lower body sensor includes a load cell.

18. The system of claim 16, wherein the lower body sensor includes at least one of a pressure sensor or a LiDAR sensor.

19. A method for tracking movement of a limb of a body, the method comprising:
receiving first outputs from an encoder system coupled to the limb;
determining a position of the limb relative to the body based on first outputs received;
receiving a second output from a load sensor carried by the body;
determining a load of the body based on the received second output;
receiving third outputs from a pressure sensor carried by the body;
determining a foot position by detecting a position of a left foot of the body relative to a position of a right foot of the body based on the third outputs from the pressure sensor;
comparing the determined position of the limb and a position threshold associated with the determined load and the determined foot position;
determining if the determined position exceeds the position threshold; and
generating a warning signal if the determined position exceeds the position threshold.

20. The method of claim 19, wherein the generating of the warning signal includes generating at least one of a sound signal, a haptic signal, or a light signal.

21. The system of claim 1, wherein the processor circuitry is to generate a warning signal if the position of the limb exceeds the position threshold.

* * * * *